US008178529B2

(12) United States Patent
Arvidsson et al.

(10) Patent No.: US 8,178,529 B2
(45) Date of Patent: May 15, 2012

(54) IMIDAZOLE SUBSTITUTED PYRIMIDINES

(75) Inventors: Per I Arvidsson, Södertälje (SE);
Jeremy Nicholas Burrows, Macclesfield (GB); Ulrika Yngve, Södertälje (SE);
Erica Tjerneld, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 50 days.

(21) Appl. No.: 12/759,869

(22) Filed: Apr. 14, 2010

(65) Prior Publication Data

US 2010/0267723 A1    Oct. 21, 2010

Related U.S. Application Data

(60) Provisional application No. 61/169,409, filed on Apr. 15, 2009.

(51) Int. Cl.
*A61K 31/506*    (2006.01)
*C07D 413/14*    (2006.01)

(52) U.S. Cl. .................................. 514/235.8; 544/122

(58) Field of Classification Search .............. 544/122
See application file for complete search history.

(56) References Cited

U.S. PATENT DOCUMENTS 6,835,726 B2    12/2004    Cushing et al.

FOREIGN PATENT DOCUMENTS

| WO | 0114375 A1 | 3/2001 |
|---|---|---|
| WO | 0220512 A1 | 3/2002 |
| WO | 0222597 A1 | 3/2002 |
| WO | 02064586 A2 | 8/2002 |
| WO | 02065979 A2 | 8/2002 |
| WO | 02066480 A2 | 8/2002 |
| WO | 03037891 A1 | 5/2003 |
| WO | 03076433 A1 | 9/2003 |
| WO | 03076434 A1 | 9/2003 |
| WO | 03076435 A1 | 9/2003 |
| WO | 03076436 A1 | 9/2003 |
| WO | 2004005283 A1 | 1/2004 |
| WO | 2004043953 A1 | 5/2004 |
| WO | 2004056368 A1 | 7/2004 |
| WO | 2004072063 A1 | 8/2004 |
| WO | 2004083203 A1 | 9/2004 |
| WO | 2004101549 A1 | 11/2004 |
| WO | 2005012298 A1 | 2/2005 |
| WO | 2005075461 A1 | 2/2005 |
| WO | 2006064251 A1 | 6/2006 |
| WO | 2006095159 A1 | 9/2006 |
| WO | 2007015064 A1 | 2/2007 |
| WO | 2007040436 A1 | 4/2007 |
| WO | 2007040440 A1 | 4/2007 |
| WO | 2007138268 A1 | 12/2007 |
| WO | 2007138277 A1 | 12/2007 |
| WO | 2007148070 A1 | 12/2007 |
| WO | 2008002244 A2 | 1/2008 |
| WO | 2008002245 A2 | 1/2008 |
| WO | 2008057933 A2 | 5/2008 |
| WO | 2009017453 A1 | 2/2009 |
| WO | 2009017454 A1 | 2/2009 |
| WO | 2009017455 A1 | 2/2009 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Bhat et. al., "Regulation and localization of tyrosine216 phosphorylation of glycogen synthase kinase-3β in cellular and animal models of neuronal degeneration", PNAS 2000, 97: 11074-11079.
Cline et al., "Effects of a Novel Glycogen Synthase Kinase-3 Inhibitor on Insulin-Stimulated Glucose Metabolism in Zucker Diabetic Fatty (fa/fa) Rats", Diabetes, 2002, 51: 2903-2910.
Cotter et al., "Abnormalities of Wnt signalling in schizophrenia—evidence for neurodevelopmental abnormality", Neuroreport 1998, 9(7):1379-1383.
Gat et al., "De Novo Hair Follicle Morphogenesis and Hair Tumors in Mice Expressing a Truncated β-Catenin in Skin", Cell, 1998, 95(5): 605-14.
Gong et al., "Osteoporosis-Pseudoglioma Syndrome . . . ", Am. J. Hum. Genet 1996, 59, 146-151.
Gould et al., "Glycogen Synthase Kinase-3: a Putative Molecular Target for Lithium Mimetic Drugs", Neuropsychopharmacology, 2005, 30:1223-1237.
Hooper et al., "The GSK3 hypothesis of Alzheimer's disease", J. of Neurochemistry, 2008, 104(6), 1433-1439.
Hoshi et al., "Regulation of mitochondrial pyruvate dehydrogenase activity by tau protein kinase I/glycogen synthase kinase 3β in brain", PNAS 1996, 93: 2719-2723.
Imanori and Uchida, "Physiology and Pathology of Tau Protein Kinases in Relation to Alzheimer's Disease", J. Biochem. 1997, 121:179-188.
Jope et al., "Glycogen Synthase Kinase-3 (GSK3): Inflammation, Diseases, and Therapeutics", Neurochem. Res. 2007, 32, 577-595.
Kannoji et al, "GSK3β: A master switch and a promising target", Expert Opin. Ther. Targets 2008, 12, 1443-1455.
Kimura et al., "GSK-3β is Required for Memory Reconsolidation in Adult Brain", PloS ONE 2008, 3, e3540.
Kitzawa et al, "Inflammation Induces Tau Pathology in Inclusion Body Myositis Model via Glycogen Synthase Kinase-3β", Ann. Neurol. 2008, 64, 15-24.
Klein and Melton; "A molecular mechanism for the effect of lithium on development", PNAS 1996, 93:8455-8459.

(Continued)

*Primary Examiner* — Shawquia Young
(74) *Attorney, Agent, or Firm* — Kenneth F. Mitchell

(57) ABSTRACT

Imidazole substituted pyrimidines and pharmaceutically acceptable salts thereof; pharmaceutical formulations containing such pyrimidines; the use of such compounds in therapy; the use of such compounds for the treatment of conditions associated with glycogen synthase kinase-3 related disorders, such as Alzheimer's disease, as well as methods of treatment of such disorders comprising administering to subjects in need of such treatment therapeutically effective amounts of such compounds.

6 Claims, No Drawings

OTHER PUBLICATIONS

Koh et al, "Inhibition of GSK-3 reduces infarct volume and improves neurobehavioral functions", BBRC 2008, 371, 894-899.

Kozlovsky et al., "Low GSK-3β Immunoreactivity in Postmortem Frontal Cortex of Schizophrenic Patients", Am. J. Psychiatry, 2000, 157, 5: 831-833.

Li X. et al., "Regulation of mouse brain glycogen synthase kinase-3 by atypical antipsychotics", Int. J. of Neuropsychopharmacol, 2007, 10: 7-19, Epubl. 2006, May 4.

Little et al., "High Bone Density Due to a Mutation in LDL-Receptor-Related protein 5", N. Engl. J. Med., 2002, 347, 943-4.

Martin et al., "Toll-like receptor-mediated cytokine production is differentially regulated by glycogen synthase kinase 3", Nat. Immunol. 2005, 6(8): 777-784.

Miura et al, "GSK-3β, a Therapeutic Target for Cardiomyocyte Protection", Circulation Journal, vol. 73, Jul. 2009, pp. 1184-1192.

Nikoulina et al., "Potential Role of Glycogen Synthase Kinase-3 in Skeletal Muscle Insulin Resistance of Type 2 Diabetes", Diabetes Feb. 2000; 49(2): 263-71.

O'Brien et al., "Glycogen Synthase Kinase-3β Haploinsufficiency Mimics the Behavioral and Molecular Effects of Lithium", J Neurosci 2004, 24(30): 6791-6798.

Ougolkov AV and Billadeau DD, "Targeting GSK-3: a promising approach for cancer therapy?", Future Oncol. Feb. 2006;2(1):91-100.

Peineau et al., "LTP Inhbibits LTD in the Hippocampus via Regulation of GSK3β", Neuron 2007, 53, 703-717.

Phiel et al., "GSK-3alpha regulates production of Alzheimer's disease amyloid-β peptides", Nature, 2003, 423, 435-439.

Pinto et al., "Wnt control of stem cells and differentiation in the intestinal epithelium", Exp. Cell Res., 2005, 306, 357-63.

Ring et al., "Selective Glycogen Synthase Kinase 3 Inhibitors Potentiate Insulin Activation of Glucose Transport and Utilization in Vitro and in Vivo", Diabetes 2003, 52: 588-595.

Sereno et al, "A novel GSK-3β inhibitor reduces Alzheimer's pathology and rescues neuronal loss in vivo", Neurobiology of Disease, 2009, 35, 359-367.

Stambolic et al., "Lithium inhibits glycogen synthase kinase-3 activity and mimics Wingless signalling in intact cells", Curr. Biol. 1996, 68(12):1664-1668.

Su et al., "Lithium, a Common Drug for Bipolar Disorder Treatment, Regulates Amyloid-β Precursor Protein Processing", Biochemistry 2004, 43: 6899-6908.

Szczepankiewicz et al., "Association Analysis of the GSK-3β T-50C Gene Polymorphism with Schizophrenia and Bipolar Disorder", Neuropsychobiology. 2006, 53: 51-56.

Tanabe et al., "Genetic Deficiency of Glycogen Synthase Kinase-3β Corrects Diabetes in Mouse Models of Insulin Resistance",PloS Biology, 2008, 6(2), 307-318.

Wang et al, "Glycogen synthase kinase 3 in MLL leukaemia maintenance and targeted therapy", Nature 2008, 455, 1205-1209.

Wang et al., "Increased expression of the WNT antagonist sFRP-1 in glaucoma elevates intraocular pressure", J. Clin. Invest. 2008, 118, 1056-1064.

Zhou et al., "Growth control of multiple myeloma cells through inhibition of glycogen synthase kinase", 2008 Leuk. Lymphoma, 49, 1945-1953.

Tobias et al., "Novel therapeutic targets in osteoporosis", Expert Opinion on Therapeutic Targets, Feb. 2002, 6(1): 41-56.

Vijayaraghavan et al., "A Role for Phosphorylation of Glycogen Synthase Kinase-3alfa in Bovine Sperm Motility Regulation", Biology of Reproduction Jun. 2000; 62 (6):1647-54.

Cecil Textbook of Medicine, eds. Bennet, J.C. and Plum, F., 20th Edition, vol. 1, pp. 1004-1010, 1996.

Wolff, Manfred E., "Burgers Medicinal Chemistry," 5th ed., Part 1, John wiley & Sons, 1995, pp. 975-977.

Banker, G.S. et al., "Modern Pharmaceutics," 3rd ed., Marcel Dekker, NY, 1996, pp. 451 and 596.

Forde et al., Cell Mol. Life Science, 64, 1930-1944, 2007.

Maeda Y et al, "4-Acylamino-6-arylfuro[2,3-d]pyrimidines: potent and selective glycogen synthase kinase-3-inhibitors". Bioorganic & Medicinal Chemistry Letters, Pergamon, Elsevier Science, GB LNKD-DOI:10.1016/J.BMCL.2004.05.064, vol. 14, No. 15, Aug. 2, 2004, pp. 3907-3911, XP008112654 ISSN:0960-894X.

* cited by examiner

IMIDAZOLE SUBSTITUTED PYRIMIDINES

This application claims priority of U.S. Provisional Application No. 61/169,409 filed on Apr. 15, 2009, the contents of which are incorporated herein by reference.

FIELD OF THE INVENTION

The present invention relates to new compounds of formula (I) or a pharmaceutically acceptable salt thereof, to pharmaceutical formulations containing said compounds and to the use of said compounds in therapy. The present invention further relates to a process for the preparation of said compounds of formula (I).

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on serine 9 residue and inactivates it (Kannoji et al, Expert Opin. Ther. Targets 2008, 12, 1443-1455).

Alzheimer's Disease (AD) Dementias, and Taupathies.

AD is characterized by cognitive decline, cholinergic dysfunction and neuronal death, neurofibrillary tangles and senile plaques consisting of amyloid-$\beta$ deposits. The sequence of these events in AD is unclear, but is believed to be related. Glycogen synthase kinase 3$\beta$ (GSK3$\beta$), or Tau phosphorylating kinase, selectively phosphorylates the microtubule associated protein Tau in neurons at sites that are hyperphosphorylated in AD brains. Hyperphosphorylated tau has lower affinity for microtubules and accumulates as paired helical filaments, which are the main components that constitute neurofibrillary tangles and neuropil threads in AD brains. This results in depolymerization of microtubules, which leads to dying of axons and neuritic dystrophy. (Hooper et al., J. Neurochem. 2008, 104(6), 1433-1439). Neurofibrillary tangles are consistently found in diseases such as AD, amyotrophic lateral sclerosis, parkinsonism-dementia of Guam, corticobasal degeneration, dementia pugilistica and head trauma, Down's syndrome, postencephalatic parkinsonism, progressive supranuclear palsy, Niemann-Pick's Disease and Pick's Disease. Addition of amyloid-$\beta$ to primary hippocampal cultures results in hyperphosphorylation of tau and a paired helical filaments-like state via induction of GSK3$\beta$ activity, followed by disruption of axonal transport and neuronal death (Imahori and Uchida, J. Biochem. 1997, 121, 179-188), while GSK3$\alpha$ has been postulated to regulate the production of amyloid-$\beta$ itself (Phiel et al. Nature, 2003, 423, 435-439). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 1996, 93: 2719-2723). Acetyl-Co-A is critical for the synthesis of acetylcholine, a neurotransmitter with cognitive functions. Accumulation of amyloid-$\beta$ is an early event in AD. GSK transgenic mice show increased levels of amyloid-$\beta$ in brain. Also, PDAPP(APP$^{V717F}$) transgenic mice fed with lithium show decreased amyloid-$\beta$ levels in hippocampus and decreased amyloid plaque area (Su et al., Biochemistry 2004, 43, 6899-6908). Likewise, GSK3$\beta$ inhibition has been shown to decrease amyloid deposition and plaque-associated astrocytic proliferation, lower tau phosphorylation, protect against neuronal cell death, and prevent memory deficincies in a double APP$^{sw}$-tau$^{vlw}$ mouse model (Serenó et al, Neurobiology of Disease, 2009, 35, 359-367). Furthermore, GSK3 has been implicated in synaptic plasticity and memory function (Peineau et al., Neuron 2007, 53, 703-717; Kimura et al., PloS ONE 2008, 3, e3540), known to be impaired in AD patients.

In summary, GSK3 inhibition may have beneficial effects in progression as well as the cognitive deficits associated with Alzheimer's disease and other above-referred to diseases.

Acute Neurodegenerative Diseases

Growth factor mediated activation of the PI3K/Akt pathway has been shown to play a key role in neuronal survival. The activation of this pathway results in GSK3$\beta$ inhibition. GSK3$\beta$ activity is increased in cellular and animal models of neurodegeneration such as cerebral ischemia or after growth factor deprivation (Bhat et al., PNAS 2000, 97, 11074-11079). Several compounds with known GSK3$\beta$ inhibitory effect has been shown to reduce infarct volume in ischemic stroke model rats. A recent publication (Koh et al, BBRC 2008, 371, 894-899) demonstrated that GSK-3 inhibition decreased the total infarction volume and improved neurobehavioral functions by reducing ischemic cell death, inflammation, brain edema, and glucose levels, in a focal cerebral ischemia model. Thus GSK3$\beta$ inhibitors could be useful in attenuating the course of acute neurodegenerative diseases.

Bipolar Disorders (BD)

Bipolar Disorders are characterized by manic episodes and depressive episodes. Lithium has been used to treat BD based on its mood stabilizing effects. The disadvantage of lithium is the narrow therapeutic window and the danger of overdosing that can lead to lithium intoxication. The discovery that lithium inhibits GSK3 at therapeutic concentrations has raised the possibility that this enzyme represents a key target of lithium's action in the brain (Stambolic et al., Curr. Biol. 1996, 68, 1664-1668; Klein and Melton; PNAS 1996, 93, 8455-8459; Gould et al., Neuropsychopharmacology, 2005, 30, 1223-1237). GSK3 inhibitor has been shown to reduce immobilization time in forced swim test, a model to assess on depressive behavior (O'Brien et al., J Neurosci 2004, 24, 6791-6798). GSK3 has been associated with a polymorphism found in bipolar II disorder (Szczepankiewicz et al., Neuropsychobiology. 2006, 53, 51-56) Inhibition of GSK3$\beta$ may therefore be of therapeutic relevance in the treatment of BD as well as in AD patients that have affective disorders.

Schizophrenia

Accumulating evidence implicates abnormal activity of GSK3 in mood disorders and schizophrenia. GSK3 is involved in signal transduction cascades of multiple cellular processes, particularly during neural development. (Kozlovsky et al., Am. J. Psychiatry, 2000, 157, 831-833) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 1998, 9, 1379-1383). Atypical antipsychotic such as olanzapine, clozapine, quetiapine and ziprasidone, inhibits GSK3 by increasing ser9 phosphorylation suggesting that antipsychotics may exert their beneficial effects via GSK3 inhibition (Li X. et al., Int. J. of Neuropsychopharmacol, 2007, 10, 7-19).

Diabetes

Type 2 diabetes mellitus is characterized by insulin resistance and β-cell failure. Insulin stimulates glycogen synthesis in skeletal muscles via dephosphorylation and thus activation of glycogen synthase and therefore increased glucose disposal. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2), 263-71) Inhibition of GSK3 increases the activity of glycogen synthase thereby decreasing glucose levels by its conversion to glycogen. In animal models of diabetes, GSK3 inhibitors lowered plasma glucose levels up to 50% (Cline et al., Diabetes, 2002, 51: 2903-2910; Ring et al., Diabetes 2003, 52, 588-595). Moreover, results obtained by using haploinsufficient GSK3β mice on a diabetic background indicated that reduced GSK3β activity also protects from β-cell failure (Tanabe et al., PloS Biology, 2008, 6(2), 307-318 GSK3 inhibition may therefore be of therapeutic relevance in the treatment of Type I and Type II diabetes to enhance insulin sensitivity and reduce β-cell failure and therefore also relevant therapy to reduce diabetic complications like diabetic neuropathy.

Alopecia

GSK3 phosphorylates and degrades β-catenin. β-Catenin is an effector of the pathway for keratonin synthesis. β-Catenin stabilization may be lead to increase hair development. Mice expressing a stabilized β-catenin by mutation of sites phosphorylated by GSK3 undergo a process resembling de novo hair morphogenesis (Gat et al., Cell, 1998, 95, 605-14)). The new follicles formed sebaceous glands and dermal papilla, normally established only in embryogenesis. Thus, GSK3 inhibition may offer treatment for a variety of indications that lead to alopecia.

Inflammatory Disease

The discovery that GSK3 inhibitors provide anti-inflammatory effects has raised the possibility of using GSK3 inhibitors for therapeutic intervention in inflammatory diseases. (Martin et al., Nat. Immunol. 2005, 6, 777-784; Jope et al., Neurochem. Res. 2007, 32, 577-595). Inflammation is a common feature of a broad range of conditions including Alzheimer's Disease and mood disorders. A recent publication (Kitazawa et al, Ann. Neurol. 2008, 64, 15-24) indicates that GSK3β may play a role in inclusion body myositis (IBM).

Cancer

GSK3 is over expressed in ovarian, breast and prostate cancer cells and recent data suggests that GSK3β may have a role in contributing to cell proliferation and survival pathways in several solid tumor types. GSK3 plays an important role in several signal transduction systems which influence cell proliferation and survival such as WNT, PI3 Kinase and NFkB. GSK3β deficient MEFs indicate a crucial role in cell survival mediated NFkB pathway (Ougolkov A V and Billadeau D D., Future Oncol. 2006 February, 2(1), 91-100). Thus, GSK3 inhibitors may inhibit growth and survival of solid tumors, including pancreatic, colon and prostate cancer. Growth control of multiple myeloma cells has been demonstrated through inhibition of GSK3 (Zhou et al 2008 Leuk. Lymphoma, 48, 1946-1953). A recent publication (Wang et al, Nature 2008, 455, 1205-1209) demonstrated that GSK3 inhibition was efficacious in a murine model of MLL leukemia. Thus, GSK3 inhibitors may also inhibit growth and survival of hematological tumors, including multiple myeloma.

Glaucoma

There is a possibility of using GSK3 inhibitors for therapeutic treatment of glaucoma. Elevated intraocular pressure (IOP) is the most significant risk factor for the development of glaucoma, and current glaucoma therapy focuses on reducing IOP, either by reducing aqueous humor production or by facilitating aqueous humor outflow. Recently published expression profiling experiments (Wang et al., J. Clin. Invest. 2008, 118, 1056-1064) have revealed that the soluble WNT antagonist sFRP-1 is over expressed in ocular cells from glaucoma patients relative to control subjects. A functional link between WNT signaling pathways and glaucoma was provided through experiments in which addition of recombinant sFRP-1 to ex vivo-cultured human eye anterior segments resulted in a decrease in aqueous humor outflow; in addition, in vivo experiments in mice demonstrated that over expression of sFRP-1 in ocular tissues resulted in increases in intraocular pressure, an effect that was antagonized by a small-molecule GSK3 inhibitor. Taken together, the results reported by Wang et al. (2008) suggest that activation of WNT signaling via inhibition of GSK3 may represent a novel therapeutic approach for lowering intraocular pressure in glaucoma.

Pain

A recent publication (WO2008/057933) indicates that GSK3beta inhibitors may play a role in the treatment of pain, particularly neuropathic pain, by modulation of glycogenolysis or is glycolysis pathways.

Bone-Related Disorders and Conditions

Genetic studies have established a link between bone mass in humans and Wnt signaling (Gong et al., Am. J. Hum. Genet. 1996, 59, 146-51, Little et al., N. Engl. J. Med., 2002, 347, 943-4). Genetic and pharmacological manipulations of Wnt signaling in mice have since then confirmed the central role of this pathway in regulating bone formation. Of the pathways activated by Wnts, it is signaling through the canonical (i.e., Wnt/β-catenin) pathway that increases bone mass through a number of mechanisms including renewal of stem cells, stimulation of pre-osteoblast replication, induction of osteoblastogenesis, and inhibition of osteoblast and osteocyte apoptosis. Therefore, enhancing Wnt pathway signaling with GSK3 inhibitors alone or in combination with a suitable device could be used for the treatment of bone-related disorders, or other conditions which involve a need for new and increased bone formation for example osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

Regenerative Medicine

Stem-cell expansion and differentiation are required for self-renewal and maintenance of tissue homeostasis and repair. The β-catenin-mediated canonical Wnt signaling pathway has been shown to be involved in controlling stem differentiation (Pinto et al., Exp. Cell Res., 2005, 306, 357-63). A physiological Wnt response may be essential for the regeneration of damaged tissues. GSK3 inhibitors by enhancing Wnt signaling may be useful to modulate stem cell function to enhance tissue generation ex vivo or in vivo in diseases associated with tissue damage or reduced tissue repair.

WO2007/040440, published Dec. 4, 2007, relates to imidazole and phenyl substituted pyrimidine compounds that are stated to have a selective inhibiting effect at GSK3 as well as a good bioavailability.

DETAILED DESCRIPTION OF THE INVENTION

The object of the present invention is to provide a new compound having a high GSK3 inhibiting potency as well having good pan-kinase selectivity, as demonstrated through CDK2 selectivity, and good cell permeability in CaCo-2 cells.

A compound of the general formula (I)

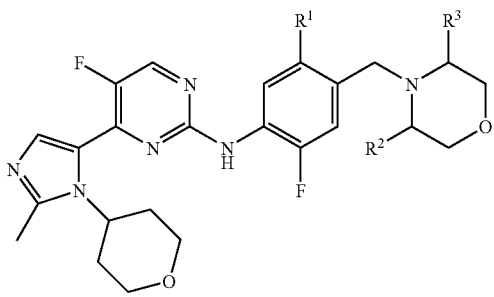

wherein
R¹ is hydrogen or fluoro;
R² and R³ are selected from hydrogen or methyl; or a pharmaceutically acceptable salt thereof.

In one aspect R¹ is fluoro; or a pharmaceutically acceptable salt thereof.

In another aspect R² and R³ are hydrogen; or a pharmaceutically acceptable salt thereof.

In a further aspect R² is methyl; or a pharmaceutically acceptable salt thereof.

In still a further aspect R² is (R)-methyl; or a pharmaceutically acceptable salt thereof.

In yet a further aspect R² and R³ are methyl; or a pharmaceutically acceptable salt thereof.

In still yet a further aspect R² and R³ are (S)-methyl; or a pharmaceutically acceptable salt thereof.

In one aspect R¹ is fluoro, R² and R³ are hydrogen; or a pharmaceutically acceptable salt thereof.

A further aspect of the invention is a compound, which is N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine; or a pharmaceutically acceptable salt thereof.

Another aspect of the invention is N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine disuccinate.

Yet another aspect of the invention is N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine hemisuccinate.

A still further aspect of the invention is a compound, which is 5-fluoro-N-(2-fluoro-4-(morpholinomethyl)phenyl)-4-(2-methyl-1-(tetrahydro-2H-pyran-4-yl)-1H-imidazol-5-yl)pyrimidin-2-amine.

N-(4-(((3S,5S)-3,5-dimethylmorpholino)methyl)-2,5-difluorophenyl)-5-fluoro-4-(2-methyl-1-(tetrahydro-2H-pyran-4-yl)-1H-imidazol-5-yl)pyrimidin-2-amine; N-(2,5-difluoro-4-(((S)-3-methylmorpholino)methyl)phenyl)-5-fluoro-4-(2-methyl-1-(tetrahydro-2H-pyran-4-yl)-1H-imidazol-5-yl)pyrimidin-2-amine; or
a pharmaceutically acceptable salt thereof.

A still further aspect of the invention is a compound, which is N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine hydrochloride; 5-fluoro-N-(2-fluoro-4-(morpholinomethyl)phenyl)-4-(2-methyl-1-(tetrahydro-2H-pyran-4-yl)-1H-imidazol-5-yl)pyrimidin-2-amine hydrochloride; 5-fluoro-N-(2-fluoro-4-(((S)-3-methylmorpholino)methyl)phenyl)-4-(2-methyl-1-(tetrahydro-2H-pyran-4-yl)-1H-imidazol-5-yl)pyrimidin-2-amine hydrochloride; N-(4-(((3S,5S)-3,5-dimethylmorpholino)methyl)-2-fluorophenyl)-5-fluoro-4-(2-methyl-1-(tetrahydro-2H-pyran-4-yl)-1H-imidazol-5-yl)pyrimidin-2-amine hydrochloride; 5-fluoro-N-(2-fluoro-4-(((R)-3-methylmorpholino)methyl)phenyl)-4-(2-methyl-1-(tetrahydro-2H-pyran-4-yl)-1H-imidazol-5-yl)pyrimidin-2-amine hydrochloride; N-(4-(((3S,5S)-3,5-dimethylmorpholino)methyl)-2,5-difluorophenyl)-5-fluoro-4-(2-methyl-1-(tetrahydro-2H-pyran-4-yl)-1H-imidazol-5-yl)pyrimidin-2-amine hydrochloride; N-(2,5-difluoro-4-(((S)-3-methylmorpholino)methyl)phenyl)-5-fluoro-4-(2-methyl-1-(tetrahydro-2H-pyran-4-yl)-1H-imidazol-5-yl)pyrimidin-2-amine hydrochloride; or as a free base or another pharmaceutically acceptable salt thereof.

A further feature of the invention relates to a compound selected from the list of all exemplified salts in their free base form or a pharmaceutically acceptable salt thereof.

Further features of the invention are the products obtainable by the processes and/or specific Examples disclosed herein.

The present invention also provides compounds selected from:
(S)-4-(4-Bromo-3-fluorobenzyl)-3-methylmorpholine;
(3S,5S)-4-(4-Bromo-3-fluorobenzyl)-3,5-dimethylmorpholine;
(R)-4-(4-Bromo-3-fluorobenzyl)-3-methylmorpholine;
(3S,5S)-4-(4-Chloro-2,5-difluorobenzyl)-3,5-dimethylmorpholine;
(S)-4-(4-Bromo-2,5-difluorobenzyl)-3-methylmorpholine;
4-Bromo-2,5-difluorobenzaldehyde;
4-(4-Chloro-2,5-difluorobenzyl)morpholine;
1-(4-Chloro-3-fluorobenzyl)-4,4-difluoropiperidine;
4-(4-Chloro-3-fluorobenzyl)morpholine;
4-(4-Bromo-3-fluorobenzyl)morpholine;
4-(4-bromo-2,5-difluorobenzyl)morpholine; or a salt thereof.
Said compounds are useful as intermediates in the process of preparing a compound is according to formula (I).

Listed below are definitions of various terms used in the specification and claims to describe the present invention.

The compounds of formula (I) may exist in stereoisomeric forms. Therefore, all enantiomers, diastereomers, racemates and mixtures thereof are included within the scope of the invention. The various optical isomers may be isolated by separation of a stereoisomeric mixture of the compounds using conventional techniques, for example, fractional crystallisation, or HPLC. Alternatively, the various optical isomers may be prepared directly using optically active starting materials.

The present invention relates to any and all stereoisomeric and tautomeric forms of the compounds of the formula (I) that possess GSK3 inhibitory activity.

The definition of compounds of formula (I) also includes solvates or solvates of salts thereof.

The present invention further includes isotopically-labeled compounds of the invention. An "isotopically" or "radiolabeled" compound is a compound of the invention where one or more atoms are replaced or substituted with an atom having an atomic mass or mass number different from the atomic mass or mass number typically found in nature (i.e., naturally occurring). Suitable stable or radioactive nuclides that may be incorporated in compounds of the present invention include but are not limited to $^2$H (also written as D for deuterium), $^3$H (also written as T for tritium) $^{11}$C, $^{13}$C, $^{14}$C, $^{13}$N, $^{15}$N, $^{15}$O, $^{17}$O, $^{18}$O, $^{18}$F, $^{35}$S $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention also relates to the use of a compound of formula (I) as hereinbefore defined.

Salts for use in pharmaceutical formulations will be pharmaceutically acceptable salts, but other salts may be useful in the production of the compounds of formula (I).

Pharmaceutical Formulations

According to one aspect of the present invention there is provided a pharmaceutical formulation comprising the compound of formula (I) or a pharmaceutically acceptable salt thereof, for use in the treatment of conditions associated with glycogen synthase kinase-3.

The formulation used in accordance with the present invention may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream, for rectal administration as a suppository and for local administration in a body cavity or in a bone cavity.

The formulation may be in a form suitable for oral administration, for example as a tablet, for parenteral injection as a sterile solution or suspension. In general the above formulation may be prepared in a conventional manner using pharmaceutically carriers or diluents.

A formulation of the invention can be in a unit dosage form such as a tablet or an injectable solution. The tablet may additionally comprise a disintegrant and/or may be coated (for example with an enteric coating or coated with a coating agent such as hydroxypropyl methylcellulose).

Suitable daily doses of the compound of formula (I) or pharmaceutically acceptable salts thereof in the treatment of a mammal, including human, are approximately 0.01 to 250 mg/kg bodyweight at per oral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

The compound of formula (I) or a pharmaceutically acceptable salt thereof, may be used on its own but will usually be administered in the form of a pharmaceutical formulation in which the active ingredient is in association with pharmaceutically acceptable diluents, excipients or inert carrier. Dependent on the mode of administration, the pharmaceutical formulation may comprise from 0.05 to 99% w (percent by weight), for example from 0.10 to 50% w, of active ingredient, all percentages by weight being based on total composition.

An example of a diluent or carrier may include one or more, but not limited to, of the following ingredients water, aqueous poly(ethylene glycol), magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

The invention further provides a process for the preparation of a pharmaceutical formulation of the invention which comprises mixing of the compound of formula (I) or a pharmaceutically acceptable salt thereof, a hereinbefore defined, with pharmaceutically acceptable diluents, excipients or inert carriers.

An example of a pharmaceutical formulations of the invention is an injectable solution to comprising the compound of formula (I) or a pharmaceutically acceptable salt thereof, as hereinbefore defined, and sterile water, and, if necessary, either a base or an acid to bring the pH of the final formulation to a pH in the range of about 4 to 9, particularly about 5, and optionally a surfactant to aid dissolution. A suitable base is sodium hydroxide. A suitable acid is hydrochloric acid.

A suitable pharmaceutically acceptable salt of the compound of formula (I) useful in accordance to the invention is, for example, an acid-addition salt, which is sufficiently basic, for example an inorganic acid such as hydrochloric acid, hydrobromic acid or sulfuric acid, or an organic acid such as succinic acid, citric acid, fumaric acid, benzoic acid, cinnamic acid, methane sulfonic acid, 1-hydroxy-2-naphtoic acid and 2-naphtalene sulfonic acid (for further example see Berge et al., J. Pharm. Sci. 1977, 66, 1-19, and/or Handbook of Pharmaceutical salts: Properties, Selection and Use by Stahl and Wermuth (Wiley-VCH, 2002.)

In addition a suitable pharmaceutically acceptable salt of the compounds of the invention, which is sufficiently acidic, is an alkali metal salt, an alkaline earth metal salt or a salt with an organic base, which affords a physiologically-acceptable cation.

It will be understood that certain compounds of the formula (I) may exist in solvated, for example hydrated, as well as unsolvated forms. It is to be understood that the present invention encompasses all such solvated forms that possess GSK3 inhibitory activity.

Medical Uses

It has been found that the compound of formula (I) defined in the present invention, are well suited for inhibiting glycogen synthase kinase-3 (GSK3). Accordingly, said compound of the present invention is expected to be useful in the prevention and/or treatment of conditions associated with glycogen synthase kinase-3 activity, i.e. the compounds may be used to produce an inhibitory effect of GSK3 in mammals, including human, in need of such prevention and/or treatment.

GSK3 is highly expressed in the central and peripheral nervous system and in other tissues. Thus, it is expected that the compound of the invention is well suited for the prevention and/or treatment of conditions associated with glycogen synthase kinase-3 in the central and peripheral nervous system. In particular, the compound of the invention is expected to be suitable for prevention and/or treatment of conditions associated with cognitive disorder(s) or indications with deficit(s) in cognition such as: dementia; incl. pre-senile dementia (early onset Alzheimer's Disease); senile dementia (dementia of the Alzheimer's type); Alzheimer's Disease (AD); Familial Alzheimer's disease; Early Alzheimer's disease; mild to moderate dementia of the Alzheimer's type; delay of disease progression of Alzheimer's Disease; neurodegeneration associated with Alzheimer's disease, Mild Cognitive Impairment (MCI); Amnestic Mild Cognitive Impairment (aMCI); Age-associated Memory Impairment (AAMI); Lewy body dementia; vascular dementia (VD); HIV-dementia; AIDS dementia complex; AIDS—Neurological Complications; Frontotemporal dementia (FTD); Frontotemporal dementia Parkinson's Type (FTDP); dementia pugilistica; dementia due to infectious agents or metabolic disturbances; dementia of degenerative origin; dementia—Multi-Infarct; memory loss; cognition in Parkinson's Disease; cognition in multiple sclerosis; cognition deficits associated with chemotherapy; Cognitive Deficit in Schizophrenia (CDS); Schizoaffective disorders including schizophrenia; Age-Related Cognitive Decline (ARCD); Cognitive Impairment No Dementia (CIND); Cognitive Deficit arising from stroke or brain ischemia; Congenital and/or development disorders; progressive supranuclear palsy (PSP); amyotrophic lateral sclerosis (ALS); corticobasal degeneration (CBD); traumatic brain injury (TBI); postencephalitic parkinsonism; Pick's Disease; Niemann-Pick's Disease; Down's syndrome; Huntington's Disease; Creuztfeld-Jacob's disease; prion diseases; multiple sclerosis (MS); motor neuron diseases (MND); Parkinson's Disease (PD); β-amyloid angiopathy; cerebral amyloid angiopathy; Trinucleotide Repeat Disorders; Spinal Muscular Atrophy; Friedreich's Ataxia; Neuromyelitis Optica; Multiple System Atrophy; Transmissible Spongiform Encephalopathies; Attention Deficit Disorder (ADD); Attention Deficit Hyperactivity Disorder (ADHD); Bipolar Disorder (BD) including acute mania, bipolar depression, bipolar maintenance; Major Depressive Disorders (MDD) including depression, major depression, mood stabilization, dysthymia; agnosia; aphasia; apraxia; apathy.

One embodiment of the invention relates to the prevention and/or treatment of Alzheimer's Disease, especially the use in the delay of the disease progression of Alzheimer's Disease.

Other embodiments of the invention relate to the prevention and/or treatment of disorders selected from the group consisting of attention deficit disorder (ADD), attention deficit hyperactivity disorder (ADHD) and affective disorders, wherein the affective disorders are Bipolar Disorder including acute mania, bipolar depression, bipolar maintenance, major depressive disorders (MDD) including depression, major depression, mood stabilization, schizoaffective disorders including schizophrenia, and dysthymia.

Other aspects of the compound of the invention is its use for treatment of Type I diabetes, Type II diabetes, diabetic neuropathy; pain including neuropathic pain, nociceptive pain, chronic pain, pain associated with cancer, pain associated with rheumatic disease; alopecia; glaucoma; inflammatory diseases; incl. inclusion body myositis (IBM); pemphigus vulgaris.

Another aspect of the compound of the invention is its use for treatment of benign or malignant tumours incl. non-solid tumours such as leukaemia including MLL leukemia; myeloma including multiple myeloma; or lymphoma; and solid tumours, for example bile duct, bone, bladder, brain/CNS, breast, colorectal, endometrial, gastric, head and neck, hepatic, lung particularly, non-small-cell lung), neuronal, oesophageal, ovarian, pancreatic, prostate, renal, skin, testicular, thyroid, uterine and vulval cancers.

Yet another aspect of the compound of the invention is its use for treatment of bone related effects of specific cancers for example breast, prostate, lung cancer, multiple myeloma, osteosarcoma, Ewing's sarcoma, chondrosarcoma, chordoma, malignant fibrous histiocytoma of bone, fibrosarcoma of bone, cancer induced bone disease and iatrogenic bone disease.

A further aspect of the compound of the invention is its use for treatment of osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease, for promoting bone formation, increasing bone mineral density, reducing the rate of fracture and/or increasing the rate of fracture healing, increasing cancellous bone formation and/or new bone formation.

The present invention relates also to the use of the compound of formula (I) as defined in the present invention in the manufacture of a medicament for the prevention and/or treatment of conditions associated with glycogen synthase kinase-3.

The invention also provides for a method of treatment and/or prevention of conditions associated with glycogen synthase kinase-3 comprising administering to a mammal, including human in need of such treatment and/or prevention a therapeutically effective amount of the compound of formula (I) as as defined in the present invention.

The dose required for the therapeutic or preventive treatment of a particular disease will necessarily be varied depending on the host treated, the route of administration and the severity of the illness being treated.

For veterinary use the amounts of different components, the dosage form and the dose of the medicament may vary and will depend on various factors such as, for example the individual requirement of the animal treated.

In the context of the present specification, the term "therapy" or "treatment" also includes "prevention" unless there are specific indications to the contrary. The terms "therapeutic" and "therapeutically" should be construed accordingly.

In the context of the present specification, the term "disorder" also includes "condition" unless there are specific indications to the contrary.

Another aspect of the invention is wherein a compound of formula (I) or a pharmaceutically acceptable salt thereof as defined herein, or a pharmaceutical composition or formulation comprising a combination comprising such a compound of formula (I) is administered, concurrently, simultaneously, sequentially, separately or adjunct with another pharmaceutically active compound or compounds selected from the following:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine; and equivalents and pharmaceutically active isomer(s) and metabolite(s) thereof.

(ii) atypical antipsychotics including for example quetiapine; and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone; and equivalents and pharmaceutically active isomer(s) and metabolite(s) thereof.

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam; and equivalents and pharmaceutically active isomer(s) and metabolite(s) thereof.

(v) anticonvulsants including for example carbamazepine, clonazepam, ethosuximide, felbamate, fosphenyloin, gabapentin, lacosamide, lamotrogine, levetiracetam, oxcarbazepine, phenobarbital, phenyloin, pregabaline, rufinamide, topiramate, valproate, vigabatrine, zonisamide; and equivalents and pharmaceutically active isomer(s) and metabolite(s) thereof.

(vi) Alzheimer's therapies including for example donepezil, rivastigmine, galantamine, memantine; and equivalents and pharmaceutically active isomer(s) and metabolite(s) thereof.

(vii) Parkinson's therapies including for example levodopa, dopamine agonists such as apomorphine, bromocriptine, cabergoline, pramipexol, ropinirole, and rotigotine, MAO-B inhibitors such as selegeline and rasagiline, and other dopaminergics such as tolcapone and entacapone, A-2 inhibitors, dopamine reuptake inhibitors, NMDA antagonists, Nicotine agonists, and inhibitors of neuronal nitric oxide synthase; and equivalents and pharmaceutically active isomer(s) and metabolite(s) thereof.

(viii) migraine therapies including for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan; and equivalents and pharmaceutically active isomer(s) and metabolite(s) thereof.

(ix) stroke therapies including for example thrombolytic therapy with eg activase and desmoteplase, abciximab, citicoline, clopidogrel, eptifibatide, minocycline; and equivalents and pharmaceutically active isomer(s) and metabolite(s) thereof.

(x) urinary incontinence therapies including for example darafenacin, falvoxate, oxybutynin, propiverine, robalzotan, solifenacin, tolterodine; and equivalents and pharmaceutically active isomer(s) and metabolite(s) thereof.

(xi) neuropathic pain therapies including lidocain, capsaicin, and anticonvulsants such as gabapentin, pregabalin, and antidepressants such as duloxetine, venlafaxine, amitriptyline, klomipramine; and equivalents and pharmaceutically active isomer(s) and metabolite(s) thereof.

(xii) nociceptive pain therapies including paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol; and equivalents and pharmaceutically active isomer(s) and metabolite(s) thereof.

(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem; and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil; and equivalents and pharmaceutically active isomer(s) and metabolite(s) thereof.

Such combination products employ the compound of this invention within the dosage range described herein and the other pharmaceutically active compound or compounds within approved dosage ranges and/or the dosage described in the publication references.

In one embodiment of the invention the combination comprises the group of compounds (a) and (b) as defined below:
(a) a first therapeutic agent, which is a GSK3 inhibitor and (b) a second therapeutic agent, which is an antipsychotic selected from:
(a) N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) quetiapine.

(a) a first therapeutic agent, which is a GSK3 inhibitor and (b) a second therapeutic agent, which is a α7-nicotinic agonist selected from:
(a) N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) (R)-5-(5-(morpholinomethyl)furan-3-yl)-3H-1'-azaspiro[furo[2,3-b]pyridine-2,3'-bicyclo[2.2.2]octane].
(a) N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) ((−)-spiro[1-azabicyclo[2.2.2]octane-3,2'-(2',3'-dihydrofuro[2,3-B]pyridine)];

The combination may employ any alpha-7 agonist, including but not limited to those disclosed in U.S. Pat. Nos. 6,110,914 and 6,569,865; and pending US Application 2008-0139600 (A1), WO96/06098, WO99/03859, WO00/42044, WO01/060821, WO02/096912, WO03/087103, WO2005/030777, WO2005/030778 and WO2007/133155.

(a) a first therapeutic agent, which is a GSK3 inhibitor and (b) a second therapeutic agent, which is a an α4β2-neuronal nicotinic agonist selected from:
(a) N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) (2S)-(4E)-N-methyl-5-[3-(5-isopropoxypyridin)yl]-4-penten-2-amine;
(a) N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) 3-(5-chloro-2-furoyl)-3,7-diazabicyclo[3.3.0]octane;

α4β2-neuronal nicotinic agonist useful in the combination of the present invention are those described in U.S. Pat. No. 6,603,011, U.S. Pat. No. 6,958,399 and WO/2008/057938, which are hereby incorporated by reference. Particular nicotinic agonists are compounds N-methyl-5-[3-(5-isopropoxypyridin)yl]-4-penten-2-amine, (4E)-N-methyl-5-[3-(5-isopropoxypyridin)yl]-4-penten-2-amine and (2S)-(4E)-N-methyl-5-[3-(5-isopropoxypyridin)yl]-4-penten-2-amine, 3-(5-chloro-2-furoyl)-3,7-diazabicyclo[3.3.0]octane, metabolites or prodrugs and pharmaceutically-acceptable salts, solvates or solvated salts of any of the foregoing. The preparation of these compounds is described in said US patents.

(a) a first therapeutic agent, which is a GSK3 inhibitor and (b) a second therapeutic agent, which is a BACE inhibitor.

(a) a first therapeutic agent, which is the GSK3 inhibitor N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) a second therapeutic agent, which is a BACE inhibitor.

Drugs useful in the combination of the present invention are those that reduce or block BACE activity should therefore reduce Aβ levels and levels of fragments of Aβ in the brain, and thus slow the formation of amyloid plaques and the progression of AD or other maladies involving deposition of Aβ or fragments thereof.

(a) a first therapeutic agent, which is a GSK3 inhibitor and (b) a second therapeutic agent, which is a H3 antagonist.

(a) a first therapeutic agent, which is the GSK3 inhibitor N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) a second therapeutic agent, which is a H3 antagonist.

The histamine H3 receptor has been shown to regulate the release of pro-cognitive neurotransmitters, such as, for example, histamine and acetylcholine. Some histamine H3 ligands, such as, for example, a histamine H3 receptor antagonist or inverse agonist may increase the release of these neurotransmitters in the brain. This suggests that histamine H3 receptor inverse agonists and antagonists could be used to improve cognitive deficits associated with neurodegenerative disorders such as AD.

(a) a first therapeutic agent, which is a GSK3 inhibitor and (b) a second therapeutic agent, which is a Aβ42 inhibitor.

(a) a first therapeutic agent, which is the GSK3 inhibitor N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) a second therapeutic agent, which is a A1342 inhibitor.

Aβ42 inhibitors useful in the combination of the present invention are those affecting the γ-secretase mediated processing of APP (Aβ amyloid precursor protein) and thereby lowering the Aβ42 and Aβ40 peptides.

(a) a first therapeutic agent, which is a GSK3 inhibitor and (b) a second therapeutic agent, which is a partial agonist or antagonist of the 5-HT$_{1A}$ and/or 5-HT$_{1B}$ receptors.

(a) a first therapeutic agent, which is the GSK3 inhibitor N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine and (b) a second therapeutic agent, which is a partial agonist or antagonist of the 5-HT$_{1A}$ and/or 5-HT$_{1B}$ receptors.

A partial agonist or antagonist of the 5-HT$_{1A}$ and/or 5-HT$_{1B}$ receptors is expected to be useful in the prevention and/or treatment of conditions associated with disturbances in 5-HT signaling mediated by 5-HT$_{1A}$ and/or 5-HT$_{1B}$ receptors, i.e. such compounds may be used to produce an increased levels of acetylcholine, glutamate, serotonin in mammals, including human, in need of such prevention and/or treatment. In particular a partial agonist or antagonist of the 5-HT$_{1A}$ and/or 5-HT$_{1B}$ receptors is expected to be suitable for prevention and/or treatment of conditions associated with cognitive disorders and predemented states, especially dementia, Alzheimer's Disease (AD), The first therapeutic agent (a) as well as the second therapeutic agent (b) may be in the form of the free base or a pharmaceutically acceptable salt thereof.

Methods of Preparation

Another aspect of the present invention provides a process for preparing a compound of is formula (I), or a pharmaceutically acceptable salt thereof, which process (wherein R$^1$, R$^2$ and R$^3$ are), unless otherwise specified, as defined in formula (I) comprises of:

Process a) reaction of a pyrimidine of formula (II):

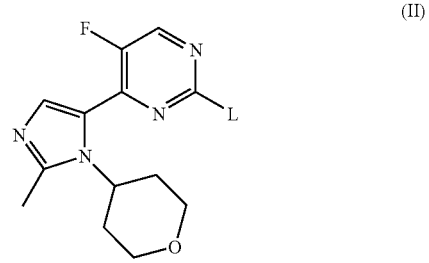

wherein L is a displaceable group; with an aniline of formula (III):

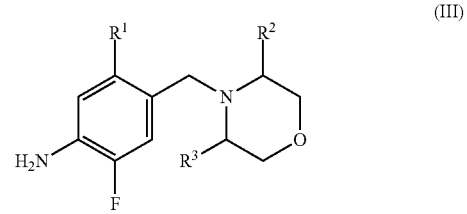

or

Process b) reacting a pyrimidine of formula (IV):

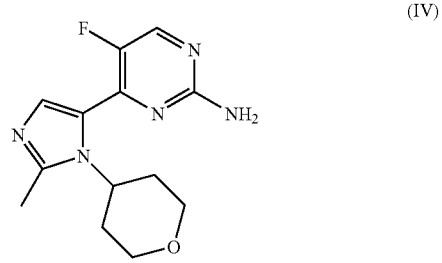

with a compound of formula (V):

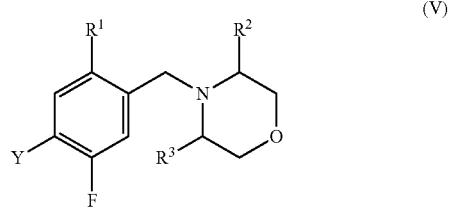

wherein Y is a displaceable group;
and thereafter if necessary:
i) converting a compound of the formula (I) into another compound of the formula (I);
ii) removing any protecting groups; and L is a displaceable group, suitable values for L are for example, a halogeno or sulphonyloxy group, for example a chloro, bromo, methanesulphonyloxy or toluene-4-sulphonyloxy group.

Y is a displaceable group, suitable values for Y are for example, a halogeno or sulphonyloxy group, for example a chloro, bromo, iodo or trifluoromethanesulphonyloxy group. Preferably Y is bromo or chloro.

Specific reaction conditions for the above reactions are as follows:

Process a) Pyrimidines of formula (II) and anilines of formula (III) may be reacted together under standard Buchwald-Hartwig conditions (for example see J. Am. Chem. Soc., 118, 7215; J. Am. Chem. Soc., 119, 8451; J. Am. Chem. Soc., 125, 6653; J. Org. Chem., 62, 1568 and 6066) for example in the presence of palladium acetate or 1,1'-bis(diphenylphosphino)ferrocene)-dichloropalladium(II), in a suitable solvent for example an aromatic solvent such as toluene, benzene or xylene or an aprotic organic solvent such as 1,4-dioxane, with a suitable base for example an inorganic base such as caesium carbonate or an organic base such as potassium-t-butoxide, in the presence of a suitable ligand such as 2,2'-bis(diphenylphosphino)-1,1'-binaphthyl or 2-dicyclohexylphosphino-2',4',6'-triiso-propyl-1,1'-biphenyl and at a temperature in the range of about +25 to about +120° C.

Pyrimidines of the formula (II), in which L is chloro, may be prepared according to the procedure described in WO 2007/040440.

Anilines of formula (III) are commercially available compounds, or these are known in the literature, or these are prepared by standard processes known in the art.

Process b) Compounds of formula (IV) and amines of formula (V) may be reacted together under standard Buchwald conditions as described in Process a.

A synthesis of pyrimidines of formula (IV) is described in WO 2007/040440.

Compounds of formula (V) are commercially available compounds, or these are known in the literature, or these are prepared by standard processes known in the art.

Preparation of Starting Materials

The starting materials for the Examples are either commercially available or prepared by standard methods from known materials. 5-Fluoro-4-(2-methyl-1-(tetrahydro-2H-pyran-4-yl)-1H-imidazol-5-yl)pyrimidin-2-amine may be prepared as described in WO2007/040440; Example 7(e). For example, the following reactions are an illustration, but not a limitation, of some of the starting materials used in the Examples.

Method 1

(S)-4-(4-Bromo-3-fluorobenzyl)-3-methylmorpholine

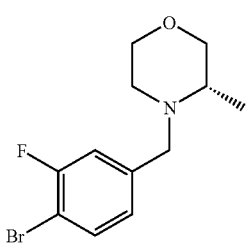

(S)-3-Methylmorpholine (119 mg, 0.86 mmol), 4-bromo-3-fluorobenzaldehyde (175 mg, 0.86 mmol) triethylamine (132 μl, 0.95 mmol) and sodium triacetoxyborohydride (274 mg, 1.29 mmol) were dissolved in dichloroethane (2.5 ml). The mixture was stirred at ambient temperature under argon atmosphere for 24 h. Hydrochloric acid (1M) was added until pH 1-2. The mixture was washed with dichloromethane. The aqueous phase was made alkaline with KOH (1M, aq) and extracted with dichloromethane. The combined organic phases were dried over $Na_2SO_4$ and concentrated in vacuo to give (S)-4-(4-bromo-3-fluorobenzyl)-3-methylmorpholine (220 mg, 89%).

$^1$H NMR (500 MHz, DMSO-$d_6$) δ ppm 7.64 (t, 1H) 7.31 (dd, 1H) 7.13 (dd, 1H) 3.92 (m, 1H) 3.62 (m, 2H) 3.43 (td, 1H) 3.15 (m, 2H) 2.39 (ddd, 1H) 2.11 (ddd, 1H) 0.97 (d, 3 H).

MS (ES$^+$) m/z 288 (M+H)$^+$.

Method 2

(3S,5S)-4-(4-Bromo-3-fluorobenzyl)-3,5-dimethylmorpholine

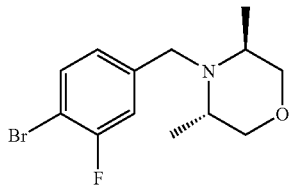

4-Bromo-3-fluorobenzaldehyde (0.250 g, 1.23 mmol) and (3S,5S)-3,5-dimethylmorpholine (0.205 g, 1.35 mmol) were dissolved in dichloromethane (10 mL). Sodium triacetoxyborohydride (0.378 g, 1.79 mmol) was added and the mixture was stirred under argon atmosphere at RT for 20 h. The mixture was diluted with dichloromethane and washed with $NaHCO_3$ (aq). The organic phase was dried (MgSO$_4$) and evaporated. The residue was purified by column chromatography on silica eluting with gradients of ammonia in methanol and dichloromethane. The fractions containing product were pooled and evaporated to give (3S,5S)-4-(4-bromo-3-fluorobenzyl)-3,5-dimethylmorpholine (0.113 g, 30%) as a liquid.

$^1$H NMR (500 MHz, CHLOROFORM-d) δ ppm 7.46 (m, 1H) 7.21 (dd, 1H) 7.04 (m, 1H) 3.88 (d, 1H) 3.69 (dd, 2H) 3.38 (m, 3H) 2.81 (m, 2H) 0.99 (d, 6H).

MS (ES$^+$) m/z 302 (M+H)$^+$.

Method 3

(R)-4-(4-Bromo-3-fluorobenzyl)-3-methylmorpholine

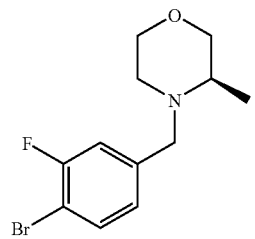

The title compound was prepared according to the procedure described in method 1 to give (R)-4-(4-bromo-3-fluorobenzyl)-3-methylmorpholine (200 mg, 81%) as a liquid.

$^1$H NMR (500 MHz, DMSO-$d_6$) δ ppm 7.64 (t, 1H) 7.31 (dd, 1H) 7.13 (dd, 1H) 3.92 (d, 1H) 3.62 (dd, 2H) 3.43 (td, 1H) 3.15 (m, 2H) 2.39 (m, 1H) 2.11 (ddd, 1H) 0.97 (d, 3H).

MS (ES+) m/z 288 (M+H)$^+$.

Method 4

(3S,5S)-4-(4-Chloro-2,5-difluorobenzyl)-3,5-dimethylmorpholine

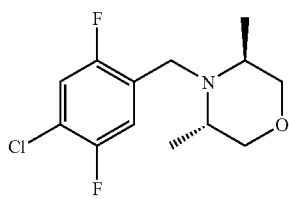

4-Chloro-2,5-difluorobenzaldehyde (0.177 g, 1.0 mmol) and (3S,5S)-3,5-dimethylmorpholine (0.167 g, 1.10 mmol) were dissolved in dichloromethane (10 mL). Sodium triacetoxyborohydride (0.307 g, 1.45 mmol) was added and the mixture was stirred under argon atmosphere at RT for 20 h. The mixture was diluted with dichloromethane and washed with $NaHCO_3$ (aq). The organic phase was dried ($MgSO_4$) and evaporated. The residue was purified by column chromatography on silica eluting with gradients of ammonia in methanol and dichloromethane. The fractions containing product were pooled and evaporated to give (3S,5S)-4-(4-chloro-2,5-difluorobenzyl)-3,5-dimethylmorpholine (0.118 g, 43%) as a liquid.

$^1$H NMR (400 MHz, CHLOROFORM-d) δ ppm 7.39 (dd, 1H) 7.11 (m, 1H) 3.80 (d, 1H) 3.71 (dd, 2H) 3.53 (d, 1H) 3.40 (dd, 2H) 2.85 (m, 2H) 1.01 (d, 6H)

MS (ES$^+$) m/z 276 (M+H)$^+$.

Method 5

(S)-4-(4-Bromo-2,5-difluorobenzyl)-3-methylmorpholine

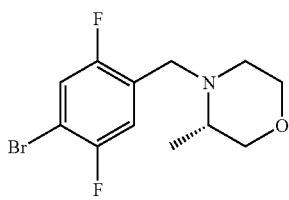

4-Bromo-2,5-difluorobenzaldehyde (331 mg, 1.5 mmol), (S)-3-methylmorpholine hydrochloride (206 mg, 1.50 mmol) and sodium triacetoxyborohydride (461 mg, 2.18 mmol) were mixed in dichloroethane (5 mL). Triethylamine (0.230 mL, 1.65 mmol) was added and the resulting mixture was stirred at RT under argon atmosphere for 24 h. $NaHCO_3$ (25 mL) was added and the mixture was extracted with dichloromethane (3×25 mL). The combined organic extracts were dried over $MgSO_4$, filtered and concentrated to give (S)-4-(4-bromo-2,5-difluorobenzyl)-3-methylmorpholine (432 mg, 94%) as a solid.

$^1$H NMR (500 MHz, CHLOROFORM-d) δ ppm 7.22-7.32 (m, 2H, overlapping with residual CHCl$_3$) 3.88 (d, 1H) 3.69-3.78 (m, 2H) 3.58-3.65 (m, 1H) 3.26-3.34 (m, 2H) 2.58-2.64 (m, 1H) 2.54 (d, 1H) 2.25-2.33 (m, 1H) 1.05 (d, 3H).

MS (ES$^+$) m/z 306 (M+H)$^+$.

Method 6

4-Bromo-2,5-difluorobenzaldehyde

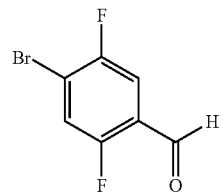

To 1,4-dibromo-2,5-difluorobenzene (10.28 g, 37.81 mmol) in tetrahydrofuran (80 mL) at −40° C. was isopropylmagnesium chloride lithium chloride complex (29.1 mL, 37.81 mmol) added dropwise. After 1 h at −40° C. was N,N-dimethylformamide (58 mL, 756 mmol) added and the mixture was stirred for 30 minutes at −40° C. $NH_4Cl$ (2M, aq, 100 mL) was added and the mixture was extracted with ethyl acetate. The organic phase was dried with $MgSO_4$ and concentrated to give 4-bromo-2,5-difluorobenzaldehyde (6.20 g, 74%) as a solid.

$^1$H NMR (500 MHz, CHLOROFORM-d) δ ppm 10.28 (d, 1H) 7.61 (dd, 1H) 7.48 (dd, 1H).

Method 7

4-(4-Chloro-2,5-difluorobenzyl)morpholine

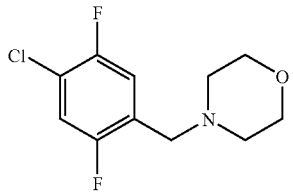

4-Chloro-2,5-difluorobenzaldehyde (1 g, 5.66 mmol), morpholine (0.490 ml, 5.66 mmol) and sodium triacetoxyborohydride (1.741 g, 8.21 mmol) were mixed in dichloroethane (17 ml). The mixture was stirred at ambient temperature under argon atmosphere for 3 days. $NaHCO_3$ (aq., sat, 25 ml) was added. The mixture was extracted with dichloromethane (×3). The combined organic phase were dried over $MgSO_4$ filtered and concentrated in vacuo to give 4-(4-chloro-2,5-difluorobenzyl)morpholine (0.600 g, 43%) as a liquid.

$^1$H NMR (500 MHz, CHLOROFORM-d) δ ppm 7.27 (m, 1H, overlapping with residual CHCl$_3$) 7.13 (m, 1H) 3.73 (m, 4H) 3.52 (s, 2H) 2.48 (m, 4H).

MS (ES+) m/z 248 (M+H)$^+$.

Method 8

4-(4-Chloro-3-fluorobenzyl)morpholine

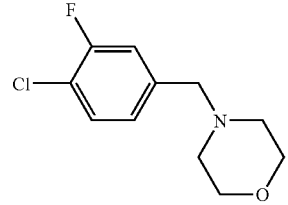

4-Chloro-3-fluorobenzaldehyde (1.0 g, 6.31 mmol), morpholine (0.546 ml, 6.31 mmol) and sodium triacetoxyborohydride (1.938 g, 9.14 mmol) were mixed in dichloroethane (19 ml) and the reaction stirred at ambient temperature under an atmosphere of argon over night. 1M HCl (aq, 25 ml) was added. The mixture was extracted with dichloromethane (×4). The pH was adjusted to ca 12 by adding KOH (s). The mixture was extracted with dichloromethane (×4). The combined organic phases were dried over MgSO₄ filtered and concentrated in vacuo to give 4-(4-chloro-3-fluorobenzyl)morpholine (0.875 g, 60%) as a liquid.

¹H NMR (500 MHz, CHLOROFORM-d) δ ppm 7.50-7.54 (m, 1H) 7.54-7.59 (m, 2H) 4.28-4.36 (m, 2H) 4.09-4.15 (m, 2H) 3.95-4.01 (m, 2H) 3.33 (d, 2H) 2.80-2.91 (m, 2H).

MS (ES⁺) m/z 230 (M+H)⁺.
Method 9

4-(4-Bromo-3-fluorobenzyl)morpholine

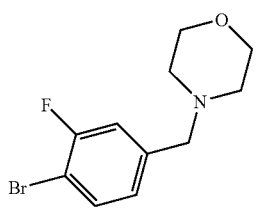

4-Bromo-3-fluorobenzaldehyde (4.69 g, 23.10 mmol) was dissolved in degassed dichloroethane (40 mL) and stirred under nitrogen. Morpholine (2.015 mL, 23.10 mmol) was added followed by sodium triacetoxyborohydride (6.37 g, 30.03 mmol) portionwise. The reaction was stirred over night. Saturated NaHCO₃ (aq) was added. The phases were separated and the organic phase was washed with 2M HCl (aq). A solid precipitated in the separation funnel. The solid was isolated by filtration. The water phase and the solid were combined and dichloromethane was added. The pH was adjusted to ca 10 by adding solid KOH. The water phase was extracted with dichloromethane (2×) and the organic phase was dried and concentrated to give 4-(4-bromo-3-fluorobenzyl)morpholine (4.45 g, 70%) as a solid.

¹H NMR (500 MHz, CHLOROFORM-d) δ ppm 7.48 (dd, 1H), 7.16 (dd, 1H), 7.00 (dd, 1 H), 3.69-3.74 (m, 4H), 3.45 (s, 2H), 2.44 (d, 4H).

MS (ES⁺) m/z 274 (M+H)⁺.
Method 10

4-(4-bromo-2,5-difluorobenzyl)morpholine

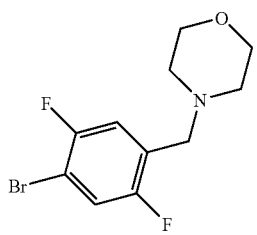

4-Bromo-2,5-difluorobenzaldehyde (15.8 g, 60.8 mmol) was dissolved in dichloromethane (150 mL) and stirred under nitrogen. Morpholine (5.83 mL, 66.9 mmol) was added followed by sodium triacetoxyborohydride (16.74 g, 79.0 mmol) portionwise (4×).

The mixture was stirred at ambient temperature over night. The reaction was quenched with saturated NaHCO₃ (aq, 80 mL). The phases were separated. To the organic phase was added hydrochloric acid (aq, 2M, 80 mL). The mixture was stirred for 20 min. A solid was isolated by filtration. To the solid was 2M NaOH (60 mL), H₂O (60 mL) and EtOAc (100 mL) added. The mixture was stirred for 15 min. The phases were separated and the organic phase was concentrated to give the title compound as a solid (17.8 g, 60.9 mmol, 100%.

1H NMR (500 MHz, DMSO-d₆) δ ppm 7.69 (dd, 5.83 Hz, 1H) 7.42 (dd, 1H) 3.53-3.60 (m, 4H) 3.48 (d, 2H) 2.30-2.47 (m, 4H).

MS (ES⁺) m/z 292 (M+H)⁺.

WORKING EXAMPLES

The following working example will describe, but not limit, the invention.

Example 1

5-Fluoro-N-(2-fluoro-4-(morpholinomethyl)phenyl)-4-(2-methyl-1-(tetrahydro-2H-pyran-4-yl)-1H-imidazol-5-yl)pyrimidin-2-amine

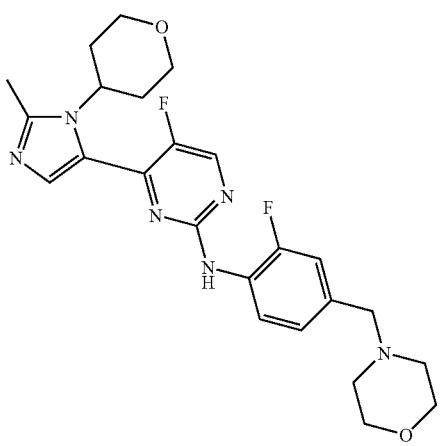

5-Fluoro-4-(2-methyl-1-(tetrahydro-2H-pyran-4-yl)-1H-imidazol-5-yl)pyrimidin-2-amine (5.12 g, 18.46 mmol), 4-(4-bromo-3-fluorobenzyl)morpholine (5.06 g, 18.46 mmol), (1,1'-bis(diphenylphosphino)ferrocene)-dichloropalladium(II) (0.152 g, 0.18 mmol), 9,9-dimethyl-4,5-bis(diphenylphosphino)xanthene (0.107 g, 0.18 mmol) and sodium tert-pentoxide (4.07 g, 36.92 mmol) in toluene (70 mL) were mixed and degassed. The mixture was stirred at 110° C. under nitrogen atmosphere overnight. The mixture was concentrated. Dichloromethane and water were added and the phases were separated. The organic phase was concentrated and the crude was purified by preparative HPLC. The pooled fractions were concentrated to about half volume. The residue was extracted with EtOAc (×2). The combined organic phases were concentrated and the residue was dried in vacuo at 40° C. for 24 h to give the title compound (5.34 g, 61%) as a solid.

¹H NMR (500 MHz, CHLOROFORM-d) ppm 8.13 (t, 1H), 7.62 (d, 1H), 7.21-7.10 (m, 2H), 7.04 (d, 1H), 5.22 (s, 1H), 4.03 (dd, 2H), 3.73 (br. s., 4H), 3.47 (s, 2H), 3.26 (t, 2H), 2.66 (s, 3H), 2.56-2.34 (m, 6H), 1.88 (dd, 2H).

MS: m/z 471 (M+H)⁺.

5-Fluoro-N-(2-fluoro-4-(morpholinomethyl)phenyl)-4-(2-methyl-1-(tetrahydro-2H-pyran-4-yl)-1H-imidazol-5-yl)pyrimidin-2-amine hydrochloride 5-Fluoro-N-(2-fluoro-4-(morpholinomethyl)phenyl)-4-(2-methyl-1-(tetrahydro-2H-pyran-4-yl)-1H-imidazol-5-yl)pyrimidin-2-amine was dissolved in dichloromethane. HCl in diethyl ether (1M, 1 equivalent) was added and the solvents were evaporated to give the title compound as a solid.

¹H NMR: (600 MHz, CD₃OD): 8.42 (d, 1H) 7.85 (t, 1H) 7.46 (d, 1H) 7.23 (d, 1H) 7.15 (d, 1H) 5.15 (tt, 1H) 3.89 (dd, 2H) 3.73 (m, 6H) 3.16 (t, 2H) 2.66 (br. s., 4H) 2.61 (s, 3H) 2.32 (m, 2H) 1.79 (dd, 2H).

MS: m/z 471 (M+H)⁺.

Example 2

5-Fluoro-N-(2-fluoro-4-(((R)-3-methylmorpholino)methyl)phenyl)-4-(2-methyl-1-(tetrahydro-2H-pyran-4-yl)-1H-imidazol-5-yl)pyrimidin-2-amine hydrochloride

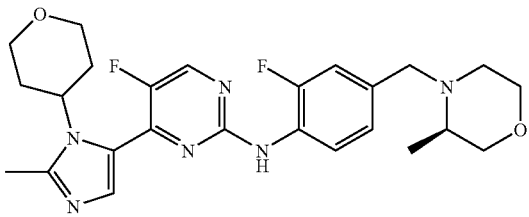

(R)-4-(4-Bromo-3-fluorobenzyl)-3-methylmorpholine (200 mg, 0.69 mmol), 5-fluoro-4-(2-methyl-1-(tetrahydro-2H-pyran-4-yl)-1H-imidazol-5-yl)pyrimidin-2-amine (192 mg, 0.69 mmol) and potassium tert-butoxide (78 mg, 0.69 mmol) were mixed in dioxane (4 ml) and the mixture was stirred under a stream of argon for 5 minutes. $Pd_2(dba)_3$ (76 mg, 0.08 mmol) and X-Phos (79 mg, 0.17 mmol) were added followed by DMF (1 ml) and the reaction mixture was heated in a microwave reactor at 120° C. for 40 minutes. The crude was filtered through diatomaceous earth. The filtrate was diluted with dichloromethane and was washed with brine. The aqueous phase was extracted with dichloromethane (×3). The organic phases were pooled, evaporated and purified by column chromatography on silica followed by preparative HPLC. Fractions containing product were pooled and KOH (aq, 20%) was added. The mixture was extracted with dichloromethane (×3). The combined organic phases were dried over $MgSO_4$ and concentrated in vacuo. The residue was dissolved in dichloromethane and HCl in ether (1M, 0.08 ml) was added. The solvents were evaporated to give the hydrochloride salt of the title compound (36 mg, 10%)

$^1$H NMR (400 MHz, MeOH) δ ppm 8.54 (d, 1H) 7.98 (t, 1H) 7.89 (d, 1H) 7.35 (d, 1H) 7.27 (d, 1H) 5.06 (m, 1H) 4.02 (d, 1H) 3.95 (m, 4H) 3.51 (t, 1H) 3.38 (m, 1H) 3.04 (m, 2H) 2.77 (s, 3H) 2.25 (m, 2H) 1.87 (m, 2H) 1.41 (d, 3H).

MS (ES$^+$): m/z 485 (M+H)$^+$.

Example 3

5-Fluoro-N-(2-fluoro-4-(((S)-3-methylmorpholino)methyl)phenyl)-4-(2-methyl-1-(tetrahydro-2H-pyran-4-yl)-1H-imidazol-5-yl)pyrimidin-2-amine hydrochloride

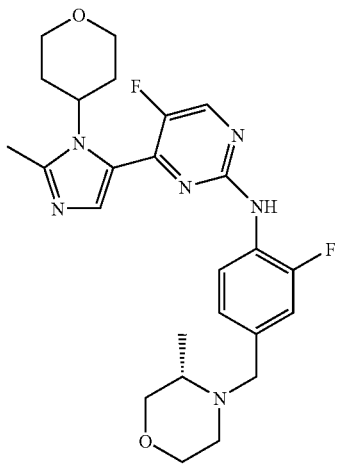

(S)-4-(4-Bromo-3-fluorobenzyl)-3-methylmorpholine (240 mg, 0.83 mmol), 5-fluoro-4-(2-methyl-1-(tetrahydro-2H-pyran-4-yl)-1H-imidazol-5-yl)pyrimidin-2-amine (231 mg, 0.83 mmol) and potassium tert-butoxide (93 mg, 0.83 mmol) were mixed in dioxane (4 ml) and the mixture was stirred under a stream of argon for 5 minutes. $Pd_2(dba)_3$ (92 mg, 0.10 mmol) and X-Phos (95 mg, 0.20 mmol) were added followed by DMF (0.5 ml) and the reaction mixture was heated in a microwave reactor at 120° C. for 40 minutes. The crude was filtered through diatomaceous earth. The filtrate was partitioned between dichloromethane and brine and the aqueous phase was extracted with dichloromethane (×3). The organic phases were pooled and evaporated. The residue was purified by preparative HPLC. Fractions containing product were pooled and 20% KOH (aq) was added. The mixture was extracted with dichloromethane (×3) and the combined organic phases were dried over $MgSO_4$ and concentrated in vacuo. The residue was dissolved in dichloromethane and HCl in ether (1M, 0.05 ml) was added. The solvents were evaporated to give the title compound (24 mg, 5.5%).

$^1$H NMR (500 MHz, DMSO-d$_6$) δ ppm 9.15 (s, 1H) 8.51 (m, 1H) 7.44 (t, 1H) 7.33 (d, 1H) 7.14 (dd, 1H) 7.08 (dd, 1H) 4.91 (m, 1H) 3.92 (d, 1H) 3.72 (m, 2H) 3.62 (m, 2H) 3.44 (dd, 1H) 3.14 (m, 2H) 2.95 (m, 2H) 2.40 (m, 1H) 2.08 (m, 3H) 1.57 (m, 2H) 1.00 (d, 3H).

MS (ES$^+$): m/z 485 (M+H)$^+$.

Example 4

N-(4-(((3S,5S)-3,5-Dimethylmorpholino)methyl)-2-fluorophenyl)-5-fluoro-4-(2-methyl-1-(tetrahydro-2H-pyran-4-yl)-1H-imidazol-5-yl)pyrimidin-2-amine hydrochloride

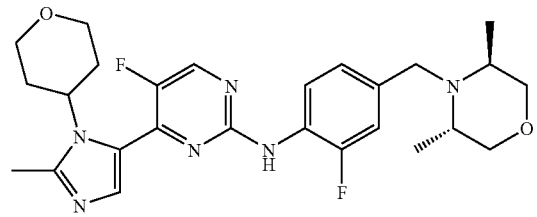

(3S,5S)-4-(4-Bromo-3-fluorobenzyl)-3,5-dimethylmorpholine (0.110 g, 0.36 mmol), 5-fluoro-4-(2-methyl-1-(tetrahydro-2H-pyran-4-yl)-1H-imidazol-5-yl)pyrimidin-2-amine (0.101 g, 0.36 mmol) and potassium tert-butoxide (0.041 g, 0.36 mmol) were mixed in dioxane (2 mL) and DMF (0.5 mL). Argon was bubbled through the mixture for 2 minutes. $Pd_2(dba)_3$ (0.040 g, 0.04 mmol) and X-Phos (0.042 g, 0.09 mmol) were added and the reaction mixture was heated in a microwave reactor at 120° C. for 40 minutes.

The mixture was diluted with dichloromethane and was filtered though a plug of diatomaceous earth. The filter plug was washed with dichloromethane and methanol. The filtrate was concentrated and purified by preparative HPLC. The fractions containing product were pooled. NaHCO$_3$ (aq) was added and the mixture was extracted with dichloromethane (×3). The combined organic phases were dried (MgSO$_4$) and evaporated. The residue was dissolved in dichloromethane (4 ml) and HCl (1M in diethyl ether, 0.1 ml) was added. The solvents were evaporated to give the title compound (35 mg, 18%) as a solid.

$^1$H NMR (400 MHz, DMSO-d$_6$) δ ppm 11.73 (br. s., 1H) 9.63 (s, 1H) 8.76 (d, 1H) 8.01 (s, 1H) 7.89 (d, 1H) 7.64 (t, 1H) 7.57 (m, 1H) 4.90 (m, 1H) 4.70 (dd, 1H) 4.07 (m, 2H) 3.91 (m, 1H) 3.73 (m, 5H) 3.56 (br. s., 1H) 3.10 (m, 3H) 2.74 (s, 3H) 2.08 (m, 2H) 1.75 (d, 2H) 1.38 (d, 3H) 1.28 (d, 3H).

MS (ES$^+$): m/z 499 (M+H)$^+$.

Example 5

N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine

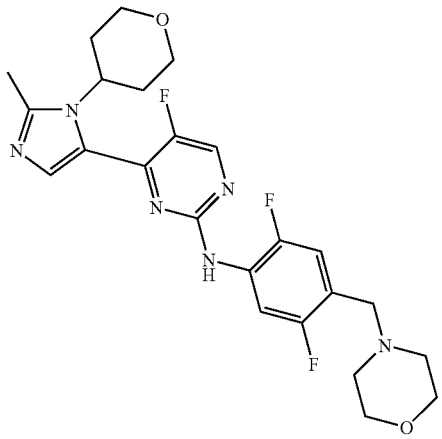

5-Fluoro-4-(2-methyl-1-(tetrahydro-2H-pyran-4-yl)-1H-imidazol-5-yl)pyrimidin-2-amine (0.876 g, 3.16 mmol), 4-(4-bromo-2,5-difluorobenzyl)morpholine (0.923 g, 3.16 mmol), Sodium tert-pentoxide (0.696 g, 6.32 mmol, (1,1'-bis (diphenylphosphino)ferrocene)-dichloropalladium(II) (0.026 g, 0.03 mmol) and (9,9-dimethyl-9H-xanthene-4,5-diyl)bis(diphenylphosphine) (0.018 g, 0.03 mmol) in toluene (10 mL) were mixed and degassed. The mixture was stirred at 110° C. under a nitrogen atmosphere overnight. The mixture was concentrated. Dichloromethane and water was added and the phases were separated. The organic phase was concentrated and the crude was purified by prep HPLC. The pooled fractions were concentrated to about half volume and the residue was extracted with EtOAc (×2). The organic phases were concentrated and the residue was dried under vacuum at 40° C. over a weekend to give the title compound (0.992 g, 64%) as a solid.

1H NMR (500 MHz, CHLOROFORM-d) ppm 8.36 (d, 1H) 8.15 (dd, 1H), 7.64 (d, 1H), 7.30 (d, 1H), 7.19 (dd, 1H), 5.20-5.33 (m, 1H), 4.09 (dd, 2H), 3.73 (t, 4H), 3.52 (s, 2H), 3.25-3.37 (m, 2H), 2.67 (s, 3H), 2.38-2.58 (m, 6H), 1.93 (dd, 2H).

MS: m/z 489 (M+H)$^+$.

N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine disuccinate 5-Fluoro-4-(2-methyl-1-(tetrahydro-2H-pyran-4-yl)-1H-imidazol-5-yl)pyrimidin-2-amine (33.6 g, 121.17 mmol), 4-(4-bromo-2,5-difluorobenzyl)morpholine (37.5 g, 128.44 mmol), (1,1'-bis(diphenylphosphino)ferrocene)-dichloropalladium(II) (0.997 g, 1.21 mmol), 9,9-dimethyl-4,5-bis(diphenylphosphino)xanthene (0.701 g, 1.21 mmol) and sodium tert-pentoxide (20.02 g, 181.75 mmol) were mixed in toluene (260 mL). The mixture was heated at 100° C. for 24 h under argon atmosphere. 4-(4-Bromo-2,5-difluorobenzyl)morpholine (4.0 g, 13.7 mmol) was added and the mixture was heated at 100° C. for 40 h under argon atmosphere.

The mixture was allowed to warm to room temperature. Water (100 mL) was added. The mixture was concentrated by evaporation. Dichloromethane (250 ml+250 ml) was added. The mixture was washed with water (2×250 mL). The organic phase was concentrated by evaporation. The residue was dissolved in EtOAc (400 mL), citric acid (2M, aq, 500 mL) was added and the mixture was stirred vigorously at room temperature for 30 min. The phases were separated and the organic phase was extracted with citric acid (2M, aq, 100 mL). The combined aqueous phases were basified with solid KOH pellets to pH 10-11 and extracted with EtOAc (5×200 mL). The combined organic phases were washed with brine, is dried (MgSO$_4$), filtered and concentrated by evaporation to give 72 g of an oil.

The oil was dissolved in EtOAc (180 mL) and succinic acid (34.8 g, 295.10 mmol) dissolved in MeOH (280 mL) was added. The mixture was stirred at room temperature for 30 min, then heptane (300 mL) was added. The mixture was stirred vigorously at room temperature overnight. The solid formed was isolated by filtration. The solid was washed with a mixture of EtOAc:heptane 1:2 (400 mL). The solid was dried in vacuo to give the title compound as the disuccinate salt (73 g, 83%).

$^1$H NMR (400 MHz, DMSO-d$_6$) δ ppm 12.16 (br. s., 4H) 9.32 (s, 1H) 8.56 (d, 1H) 7.49 (dd, 1H) 7.36 (d, 1H) 7.24 (dd, 1H) 4.95 (m, 1H) 3.75 (dd, 2H) 3.56 (t, 4H) 3.46 (s, 2H) 2.99 (t, 2H) 2.37 (m, 4H) 2.10 (m, 2H) 1.63 (m, 2H);

MS: m/z 489 (M+H)$^+$;

Melting point. 162° C.

The solid was analysed by X-ray powder diffraction (XRPD) showing that it is crystalline. The crystallinity was analysed using the XRPD instrumentation which is a PANalytical X'Pert Pro, Bragg-Brentano, θ-θ, Cu K$_α$, rotating sample and a PIXcel detector.

The following diffractions, with measured angles given as °2θ (Cu Kα) and relative intensity are shown: 7.12 (vs), 9.41 (vs), 9.90 (s), 10.68 (vs), 12.84 (vs), 14.27 (s), 17.86 (vs), 21.45 (vs), 24.61 (s) and 25.31 (vs).

The relative intensities were derived from diffractograms measured with variable slits. The measured relative intensities vs. the strongest peak are given as very strong (vs) above 50% and as strong (s) between 25 and 50%.

The significant measured angles given as °2θ (Cu Kα) and relative intensity are: 7.12 (vs), 9.41 (vs), 9.90 (s), 12.84 (vs), and 25.31 (vs).

Even more significant measured angles given as °2θ (Cu Kα) and relative intensity are: 7.12 (vs) and 12.84 (vs).

N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine hemisuccinate N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine disuccinate (1.08 g) was slurried in a mixture of ethylacetate (10 ml) and methanol (10 ml) in room temperature for 24 hrs. The solids were filtered and dried at 40° C. in vacuo to give N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine hemisuccinate salt (0.36 g) as a crystalline solid.

Melting point: 177° C.

The solid was analysed by X-ray powder diffraction (XRPD) showing that it is crystalline.

The crystallinity was analysed using the XRPD instrumentation which is a PANalytical X'Pert Pro, Bragg-Brentano, θ-θ, Cu K$_α$, rotating sample and a PIXcel detector.

The following diffractions, with measured angles given as °2θ (Cu Kα) and relative intensity are shown: 6.84 (vs), 7.84 (vs), 11.25 (s), 13.08 (s), 13.43 (m), 16.15 (s), 16.97 (s), 19.39 (s), 19.95 (m), 21.10 (vs), 22.25 (m) and 23.92 (s).

The relative intensities were derived from diffractograms measured with variable slits. The measured relative intensities vs. the strongest peak are given as very strong (vs) above 50% and as strong (s) between 25 and 50%.

The significant measured angles given as °2θ (Cu Kα) and relative intensity are: 6.84 (vs), 7.84 (vs), 11.25 (s), 13.08 (s), 16.15 (s), 19.39 (s), 21.10 (vs) and 23.92 (s).

Even more significant measured angles given as °2θ (Cu Kα) and relative intensity are: 6.84 (vs) and 7.84 (vs).

It will be appreciated by a person skilled in the art that the XRPD intensities may vary between different samples and different sample preparations for a variety of reasons including preferred orientation. It will also be appreciated by a person skilled in the art that small shifts in the measured Angle may occur for a variety of reasons including variation of sample surface level in the diffractometer, variations in peak settings both from automatic and manual judgments. The values are not to be seen as absolute.

Differential scanning calorimetry (DSC) was performed under nitrogen in aluminium sample cups with perforated lids using a Netzsch DSC 204 instrument. The scan rate was 10° C. per minute. The sample size was about 2 mg.

The melting point determined as the onset of the melting endotherm, sometimes referred to as the extrapolated onset.

It is well known that the DSC onset and peak temperatures as well as energy values may vary due to, for example, the purity of the sample and sample size and due to instrumental parameters, especially the temperature scan rate. Hence the DSC data presented are not to be taken as absolute values.

A person skilled in the art can set up instrumental parameters for a Differential scanning calorimeter so that data comparable to the data presented here can be collected according to standard methods, for example those described in Höhne, G. W. H. et al (1996), Differential Scanning Calorimetry, Springer, Berlin.

Example 6

N-(2,5-Difluoro-4-(morpholinomethyl)phenyl)-5-fluoro-4-(2-methyl-1-(tetrahydro-2H-pyran-4-yl)-1H-imidazol-5-yl)pyrimidin-2-amine hydrochloride

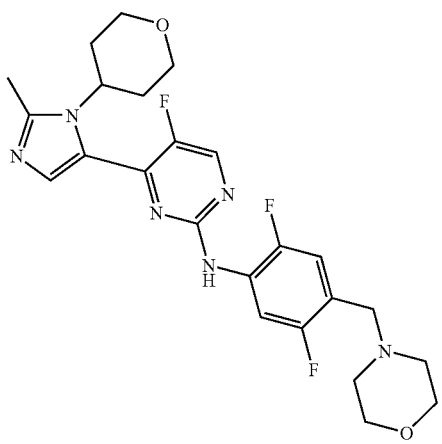

5-Fluoro-4-(2-methyl-1-(tetrahydro-2H-pyran-4-yl)-1H-imidazol-5-yl)pyrimidin-2-amine (432 mg, 1.56 mmol) was dissolved in 1,4-dioxane (18 ml) and 4-(4-chloro-2,5-difluorobenzyl)morpholine (390 mg, 1.57 mmol) and potassium tert-butoxide (230 mg, 2.05 mmol) were added. The mixture was flushed with argon and stirred for 5-10 minutes. Tris (dibenzylideneacetone)dipalladium(0) (144 mg, 0.16 mmol) and 2-dicyclohexylphosphino-2',4',6'-tri-iso-propyl-1,1'-biphenyl (150 mg, 0.31 mmol) were added. The mixture was heated at 102° C. under an atmosphere of argon for 3 h.

The crude mixture was filtered through diatomaceous earth and the filter plug was washed with dichloromethane. The solution was concentrated in vacuo and the residue was purified by preparative HPLC. The fractions containing product were pooled and $Na_2CO_3$ (aq.) was added. The mixture was extracted with dichloromethane (×3), dried over $Na_2SO_4$ and concentrated in vacuo. The residue was dissolved in dichloromethane and HCl in diethyl ether (1M) was added. The solvents were evaporated to give N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine (125 mg, 15%) as the hydrochloride salt.

$^1$H-NMR: (600 MHz, $CD_3OD$): 8.63 (br s, 1H), 8.22 (br s, 1H), 7.78 (br s, 1H), 7.42 (br s, 1H), 5.18 (m, 1H), 4.32 (s, 2H), 4.01 (dd, 2H), 3.44 (m, 1H), 3.36 (t, 3H), 3.33 (m, 4H), 3.17 (m, 1H), 2.77 (br s, 3H), 2.44 (m, 2H).

MS: m/z 489 ($M^+$+1).

Example 7

N-(2,5-Difluoro-4-(((S)-3-methylmorpholino)methyl)phenyl)-5-fluoro-4-(2-methyl-1-(tetrahydro-2H-pyran-4-yl)-1H-imidazol-5-yl)pyrimidin-2-amine

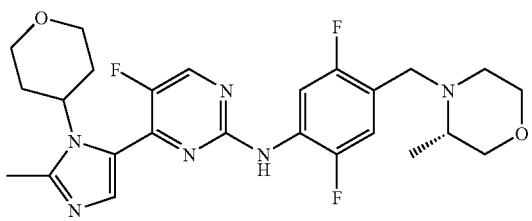

(S)-4-(4-Bromo-2,5-difluorobenzyl)-3-methylmorpholine (430 mg, 1.40 mmol), 5-fluoro-4-(2-methyl-1-(tetrahydro-2H-pyran-4-yl)-1H-imidazol-5-yl)pyrimidin-2-amine (389 mg, 1.40 mmol) and potassium tert-butoxide (158 mg, 1.40 mmol) were mixed in dioxane (7 mL) and argon was bubbled through the mixture for 5 minutes. $Pd_2(dba)_3$ (154 mg, 0.17 mmol) and X-Phos (161 mg, 0.34 mmol) were added followed by DMF (1.75 mL) and the reaction mixture was heated in a microwave reactor at 120° C. for 40 minutes.

The mixture was filtered through diatomaceous earth and the filter plug was washed with dichloromethane. The filtrate was concentrated and the residue was purified by preparative HPLC. Fractions containing product were pooled, extracted with dichloromethane (×3), dried over $MgSO_4$ and concentrated in vacuo to give the title compound as a solid (104 mg, 15%).

$^1$H NMR (500 MHz, CHLOROFORM-d) δ ppm 8.35 (d, 1H) 8.11 (dd, 1H) 7.64 (d, 1H) 7.35 (d, 1H) 7.20 (dd, 1H) 5.14-5.29 (m, 1H) 4.08 (dd, 2H) 3.89 (d, 1H) 3.68-3.79 (m, 2H) 3.57-3.66 (m, 1H) 3.24-3.37 (m, 3H) 2.68 (br. s., 1H) 2.67 (s, 2H) 2.64 (d, 1H) 2.49-2.57 (m, 1H) 2.44 (qd, 2H) 2.25-2.33 (m, 1H) 1.92 (d, 2H) 1.08 (d, 2H).

MS ($APCI^+$): m/z 503 $(M+H)^+$.

N-(2,5-Difluoro-4-(((S)-3-methylmorpholino)methyl)phenyl)-5-fluoro-4-(2-methyl-1-(tetrahydro-2H-pyran-4-yl)-1H-imidazol-5-yl)pyrimidin-2-amine hydrochloride The solid (104 mg) was dissolved in dichloromethane (2 ml) and HCl in ether (1M, 0.25 mL) was added. The solid was collected by filtration to give N-(2,5-difluoro-4-(((S)-3-methylmorpholino)methyl)phenyl)-5-fluoro-4-(2-methyl-1-(tetrahydro-2H-pyran-4-yl)-1H-imidazol-5-yl)pyrimidin-2-amine (39.0 mg) as the hydrochloride salt.

$^1$H NMR (500 MHz, DMSO-$d_6$) d ppm 11.41 (br. s., 1H) 9.81 (br. s., 1H) 8.82 (d, 1H) 8.01 (br. s., 1H) 7.75 (br. s., 2H) 4.96 (br. s., 1H) 3.90 (m, 2H) 3.83 (d, 4H) 3.15 (t, 3H) 2.76 (s, 3H) 2.13 (m, 2H) 1.83 (d, 2H) 1.40 (br. s., 3H)

MS (APCI$^+$) m/z 503 (M+H)$^+$.

Example 8

N-(4-(((3S,5S)-3,5-Dimethylmorpholino)methyl)-2,5-difluorophenyl)-5-fluoro-4-(2-methyl-1-(tetrahydro-2H-pyran-4-yl)-1H-imidazol-5-yl)pyrimidin-2-amine (3S,5S)-4-(4-Chloro-2,5-difluorobenzyl)-3,5-dimethylmorpholine (0.118 g, 0.43 mmol), 5-fluoro-4-(2-methyl-1-(tetrahydro-2H-pyran-4-yl)-1H-imidazol-5-yl)pyrimidin-2-amine (0.142 g, 0.51 mmol) and potassium tert-butoxide (0.058 g, 0.51 mmol) were mixed in dioxane (2 mL) and DMF (0.5 mL). Argon was bubbled through the mixture for 2 minutes. Pd$_2$(dba)$_3$ (0.047 g, 0.05 mmol) and X-Phos (0.049 g, 0.10 mmol) were added and the reaction mixture was heated in a microwave reactor at 120° C. for 40 minutes. The mixture was diluted with dichloromethane and was filtered though a plug of diatomaceous earth. The filter plug was washed with dichloromethane and methanol. The filtrate was concentrated and purified by preparative HPLC. The fractions containing product were pooled. NaHCO$_3$ (aq) was added and the mixture was extracted with dichloromethane (×3). The combined organic phases were dried (MgSO$_4$) and evaporated to give the title compound as a solid (16 mg, 7.2%).

$^1$H NMR (500 MHz, CHLOROFORM-d) δ ppm 8.35 (d, 1H) 8.10 (dd, 1H) 7.64 (d, 1H) 7.31 (dd, 1H) 7.25 (br. s., 1H) 5.27 (m, 1H) 4.08 (dd, 2H) 3.80 (d, 1H) 3.70 (dd, 2H) 3.52 (d, 1H) 3.40 (dd, 2H) 3.31 (t, 2H) 2.85 (m, 2H) 2.68 (s, 3H) 2.44 (qd, 2H) 2.01 (s, 1H) 1.93 (dd, 2H) 1.68 (br. s., 1H) 1.27 (m, 1H) 1.03 (d, 6H).

N-(4-(((3S,5S)-3,5-Dimethylmorpholino)methyl)-2,5-difluorophenyl)-5-fluoro-4-(2-methyl-1-(tetrahydro-2H-pyran-4-yl)-1H-imidazol-5-yl)pyrimidin-2-amine hydrochloride N-(4-(((3S,5S)-3,5-dimethylmorpholino)methyl)-2,5-difluorophenyl)-5-fluoro-4-(2-methyl-1-(tetrahydro-2H-pyran-4-yl)-1H-imidazol-5-yl)pyrimidin-2-amine (16 mg) was dissolved in dichloromethane (4 ml) and HCl (1M in diethyl ether, 0.05 ml) was added. The solvents were evaporated to give the title compound (0.015 g) as a solid.

$^1$H NMR (500 MHz, METHANOL-$d_4$) δ ppm 8.67 (d, 1H) 8.23 (br. s., 1H) 7.88 (d, 1H) 7.56 (dd, 1H) 5.18 (m, 1H) 4.01 (dd, 3H) 3.39 (t, 2H) 2.83 (s, 3H) 2.41 (m, 2H) 2.01 (m, 2H) 1.46 (br. s., 6H).

MS (ES$^+$): m/z 517 (M+H)$^+$.

General Methods $^1$H NMR spectra were recorded in the indicated deuterated solvent at 400 MHz, 500 MHz or 600 MHz. The 400 MHz spectra were obtained using a Bruker av400 NMR spectrometer equipped with a 3 mm flow injection SEI $^1$H/D-$^{13}$C probe head with Z-gradients, using a BEST 215 liquid handler for sample injection, or using a Bruker DPX400 NMR or Bruker 500 MHz ultrashield spectrometer equipped with a 4-nucleus probehead with Z-gradients. The 600 MHz spectra were obtained using a Bruker DRX600 NMR spectrometer, operating at 600 MHz for $^1$H, 150 MHz for $^{13}$C, and 60 MHz for $^{15}$N equipped with a 5 mm BBO probehead with Z-gradients. Chemical shifts are given in ppm down- and upfield from TMS. Resonance multiplicities are denoted s, d, t, q, m and br for singlet, doublet, triplet, quartet, multiplet, and broad respectively.

LC-MS analyses were recorded on a Waters LCMS equipped with a Waters X-Terra MS, C8-column, (3.5 μm, 100 mm×3.0 mm i.d.). The mobile phase system consisted of A: 10 mM ammonium acetate in water/acetonitrile (95:5) and B: acetonitrile. A linear gradient was applied running from 0% to 100% B in 4-5 minutes with a flow rate of 1.0 mL/min. The mass spectrometer was equipped with an electrospray ion source (ESI) operated in a positive or negative ion mode. The capillary voltage was 3 kV and the mass spectrometer was typically scanned between m/z 100-700. Alternative, LC-MS HPLC conditions were as follows: Column: Agilent Zorbax SB-C8 (5 μm, 50 mm×2 mm i.d) Flow: 1.0 mL/min-Gradient: 95% A to 100% B in 5 min. A=5% acetonitrile in water with 0.1% formic acid and B=acetonitrile with 0.1% formic acid. UV-DAD 210-400 nm. Alternative, LC-MS analyses were recorded on a Waters 2790 LCMS equipped with a Phenomenex Luna C18 (5 μm, 50×4.6 mm i.d.) The mobile phase system consisted of A: 10 mM ammonium formate (pH 4) in water and B: acetonitrile. A linear gradient was applied running from 95% to 5% B in 5 minutes with a flow rate of 2.0 mL/min. The mass spectrometer was equipped with an electrospray ion source (ESI) operated in a positive or negative ion mode. The capillary voltage was 3 kV and the mass spectrometer was typically scanned between m/z 100-700.

Mass spectra (MS) were run using an automated system with atmospheric pressure chemical (APCI or CI) or electrospray (+ESI) ionization. Generally, only spectra where parent masses are observed are reported. The lowest mass major ion is reported for molecules where isotope splitting results in multiple mass spectral peaks (for example when chlorine is present).

HPLC assays were performed using an Agilent HP1100 Series system equipped with a Waters X-Terra MS, C$_8$ column (3.0×100 mm, 3.5 μm). The column temperature was set to 40° C. and the flow rate to 1.0 mL/min. The Diode Array Detector was scanned from 200-300 nm. A linear gradient was applied, run from 0% to 100% B in 4 min. Mobile phase A: 10 mM ammonium acetate in water/acetonitrile (95:5), mobile phase B: acetonitrile.

HPLC purities were performed using a Dionex P680 Series system equipped with a Genesis AQ, (100×4.6 mm, 4 μm) column. The column temperature was set to 25° C. and the flow rate to 1.5 mL/min. The Diode Array Detector was scanned from 200-300 nm. The mobile phase system comprise of A: 10/90 (v/v) acetonitrile/phosphate buffer (25 mM, pH 6.8) and B: 70/30 (v/v) acetonitrile/phosphate buffer (25 mM, pH 6.8). A gradient was applied according to the table below:

| Time (min) | % B |
|---|---|
| 0 | 5 |
| 5 | 5 |
| 20 | 100 |
| 21 | 5 |
| 25 | 5 |

Preparative HPLC was performed on a Waters Auto purification HPLC-UV system with a diode array detector using a Waters XTerra® MS $C_8$ column (19×300 mm, 7 µm) with the gradient described.

The compounds have been named using CambridgeSoft MedChem ELN v2.1 or ACD/Name, version 8.08, software from Advanced Chemistry Development, Inc. (ACD/Labs), Toronto ON, Canada, www.acdlabs.com, 2004 or are according to IUPAC convention.

Pharmacology

Determination of ATP Competition in Scintillation Proximity GSK3β Assay.

The inhibition experiments were carried out in duplicate with 10 concentrations of the inhibitor in 384 well clear-bottom microtitre plates. A biotinylated peptide substrate (Biotin-Ala-Ala-Glu-Glu-Leu-Asp-Ser-Arg-Ala-Gly-Ser (PO3H2)-Pro-Gln-Leu (AstraZeneca, Lund)), was added at a final concentration of 1 mmol/L in an assay buffer (pH 7.0) containing 0.1 mU recombinant human GSK3β (Dundee University, UK), (1 nmol/L active enzyme), 10 mmol/L morpholinepropanesulfonic acid (MOPS), 0.3 mmol/L EDTA, 0.01% (v/v) β-mercaptoethanol, 0.003% (w/v) polyethylene 23 lauryl ether (Brij 35), 0.4% glycerol and 0.02 mg bovine serum albumin (BSA) and preincubated for 10 minutes. The reaction was initiated by the addition of 0.06 mCi [γ-33P]ATP (Amersham, UK) and unlabelled ATP in 30 mmol/L $Mg(Ac)_2$ to a final concentration of 1 mmol/L ATP. The final assay volume was 15 mL. Blank controls without peptide substrate were used. After incubation for 15 min at room temperature, the reaction was terminated by the addition of stop solution containing 1.3 mmol/L EDTA, 13 mmol/L ATP, 0.02% Triton™X-100 and 0.15 mg streptavidin coated SPA beads. After a 5 minutes centrifugation at 2000 rpm, the radioactivity was measured in a liquid scintillation counter (1450 MicroBeta Trilux, Perkin Elmer, Finland). The Km value of ATP for GSK3β, used to calculate the inhibition constants (Ki) of the various compounds, was 20 µM.

Determination of ATP Competition in Scintillation Proximity CDK2 Assay.

The competition experiments were carried out in duplicate with 10 concentrations of the inhibitor in 96 well clear-bottom microtiter plates. Cdk2/cyclin E enzyme was added at a concentration corresponding to a 80 times dilution of the partially purified baclulovirus infected insect cell lysate in a buffer containing 50 mmol/L HEPES, 10 mmol/L $MnCl_2$, 1 mmol/L dithiothreitol (DTT), 100 µmol/L NaF, 100 µmol/L sodium vanadate, 10 mmol/L sodium glycerophosphate, 5 µg/mL aprotinin, 2.5 µg/mL leupeptin and 100 µmol/L PMSF, pH 7.5. Blank controls without enzyme were used. The reaction was initiated by the addition of 1.25 µg GST-Rb, 0.15 µCi [γ-33P]ATP and unlabelled ATP at a final concentration of 0.1 µmol/L. The final assay volume was 50 µL. After incubation for 60 min at room temperature, each reaction was terminated by the addition of 150 µL stop solution containing 45 µL protein A coated SPA beads in 50 mmol/L HEPES, 3.28 mg antiglutathione-S-transferase, and 5.5 mmol/L EDTA and 35 µmol/L ATP. The plate was centrifuged at 2000 rpm for 5 min and the radioactivity was determined in a liquid scintillation counter (1450 MicroBeta Trilux, Perkin Elmer, Finland). The Km value of ATP for Cdk2 used to calculate the inhibition constants (Ki) of the various compounds, was 0.5 µM CaCo-2 Cell Permeability Assay CaCo-2 cells were seeded onto filter membrane at a density of 340500 cells/cm2 for 24 well plates (0.33 $cm^2$/well). The cells were grown in culture medium consisting of Dulbecco's modified Eagle's medium with glucose and L-glutamine supplemented with 10% fetal bovine serum, 100 U/ml penicillin-G, and 100 µg/ml streptomycin and 1% (v/v) 100× non-essential amino acids. The culture medium was replaced every second day and the cells were maintained at 37° C., 95% relative humidity, and 5% $CO_2$. Permeability studies were conducted with the monolayers cultured for 21-28 days with the cell passage numbers between 25 and 50.

Alt 1

The CaCo-2 Permeability Assay Used in Examples 3, 5, 6 and Reference Example

The CaCo-2 permeabilty assay were performed in the apical to basolateral directions under gradient pH-gradient conditions (pH 6.5 apically, pH 7.4 basolaterally). HBSS containing 25 mM HEPES (pH 7.4) and 25 mM MES (pH 6.5) was used as transport medium. Fully differentiated cell monolayers were washed with transport medium. The drug solutions, typically 10 µM, were prepared in transport medium, pH 6.5 (1% DMSO). The permeability experiment was started by adding 0.2 ml drug solutions on the apical side. The basolateral side contained 0.8 ml of transport medium, pH 7.4. Three inserts with cells and one without were assayed for each drug. Cells were kept in an incubator at 37° C. and shaking 200 µl samples were taken at 45 and 90 min from the basolateral side. The same volume of transport buffer was added to the basolateral compartments after the first sampling. Compound recovery was assessed by calculating the sum of the cumulatively transported amount and the amount left in the donor side against the initial amount of drug. The samples were analysed online using liquid chromatography tandem mass spectrometry (LC/MS/MS). The integrity of the monolayers was ensured by measurements of the permeability of radiolabelled mannitol (paracellular marker molecule) in each well during the experiments. The samples of 25 µl were analysed by liquid scintillation.

Alt 2

The CaCo-2 A to B Permeability Assay Used in Examples 2-4, 7-8

The CaCo-2 A to B assay was performed in the apical to basolateral direction (each in duplicates) at pH 7.4. HBSS containing 25 mM HEPES (pH 7.4) was used as transport medium. The drug solutions, typically 10 µM, were prepared in transport medium (1% DMSO). Studies of six compounds can be performed in one 24 well plate that generates one 96 deepwell analysis plate (maximum capacity 6 plates=36 compounds and 6 deep well plates). The CaCo-2 cell monolayers were washed once with HBSS for 10 minutes prior to start. Transport buffer, 800 µL, (HBSS, pH 7.4) is first dispensed to the basal side of the monolayer. The assay is then initiated by addition of 225 µL of each compound (10 µM) to the apical side. Samples are withdrawn directly (Donor 0) and at 60 min (Donor end and Receiver 60) post addition of test compound. 25 µL and 150 µL are withdrawn from the donor compartment and the receiver compartment, respectively. During washing-step and incubation with compounds the transwell plates are placed in a shaking incubator at 480 rpm and 37° C. The integrity of the epithelial cell monolayer is monitored by measuring the amount of radiolabelled [$^{14}$C]mannitol (low passive paracellular diffusion) in the donor compartment at time 0 min to 60 min. Luma Plate 96-well is used for analysis of [14C]mannitol. Compound recovery was assessed by calculating the sum of the cumulatively transported amount and the amount left in the donor side against the initial amount of drug. The samples were analysed online using liquid chromatography tandem mass spectrometry (LC/MS/MS).

The apparent permeability coefficient is calculated as follows:

$$P_{app} = \frac{\Delta Q/\Delta t}{A * C_0}$$

where $\Delta Q/\Delta t$ is the total amount of substance transported into the receiver chamber per unit time, A is the surface area (cm$^2$), and $C_0$ the starting donor concentration. The apparent permeability $P_{app}$ is expressed in $\times 10^{-6}$ cm/sec.

Results

The GSK3 $K_i$ value, CDK2 $K_i$ value, the selectivity GSK3β versus CDK2 for the compound of formula (I) of the present invention are shown in Table 1. All the values given are mean values.

The CaCo-2 $P_{app}$/CaCo-2 A to B $P_{app}$ for the compound of formula (I) of the present invention is shown in Table 2. All the values given are mean values.

TABLE 2

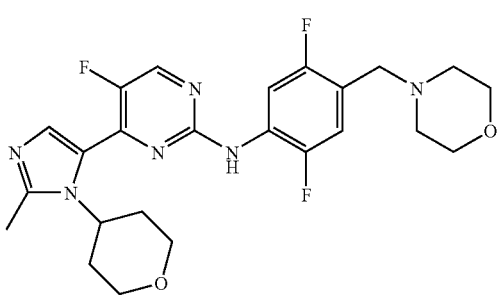

| Ex no | R$^1$ | R$^2$ (abs conf) | R$^3$ | GSK3β $K_i$ (nM) | CDK2 $K_i$ (nM) | Selectivity GSK3β vs CDK2 | CaCo-2 Papp/ A to B Papp (cm/s) |
|---|---|---|---|---|---|---|---|
| Ex 1 | H | H | H | 15 | 308 | 20 | 36 × 10$^{-6}$ |
| Ex 2 | H | CH$_3$ (R) | H | 5 | 290 | 58 | 39 × 10$^{-6}$ |
| Ex 3 | H | CH$_3$ (S) | H | 30 | 940 | 31 | 56 × 10$^{-6}$ |
| Ex 4 | H | CH$_3$ | CH$_3$ | 11 | 318 | 29 | 44 × 10$^{-6}$ |
| Ex 5 | F | H | H | 4.9 | 127 | 26 | 45 × 10$^{-6}$ |
| Ex 6 | F | H | H | 4.9 | 133 | 27 | 45 × 10$^{-6}$ |
| Ex 7 | F | CH$_3$ (S) | H | 11 | 175 | 16 | 44 × 10$^{-6}$ |
| Ex 8 | F | CH$_3$ | CH$_3$ | 7.7 | 222 | 29 | 40 × 10$^{-6}$ |

Reference example: WO2007/040440, Example 15; 5-fluoro-4-(2-methyl-1-(tetrahydro-2H-pyran-4-yl)-1H-imidazol-5-yl)-N-(4-(morpholinomethyl)phenyl)pyrimidin-2-amine

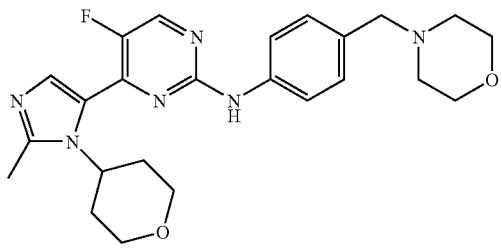

| GSK3β $K_i$ (nM) | CDK2 $K_i$ (nM) | Selectivity GSK3β vs CDK2 | CaCo-2 Papp/ A to B Papp (cm/s) |
|---|---|---|---|
| 8.1 | 110 | 14 | 26 × 10$^{-6}$ |

The following abbreviations have been used:

| | |
|---|---|
| APCI | Atmospheric Presssure Chemical Ionization |
| ATP | Adenosine Triphosphate |
| BSA | Bovin Serum Albumin |
| CaCo-2 | Human Epithelia Colorectal Adenocarcinoma Cells |
| CDK2 | Cyklin dependent kinase 2 |
| CI | Chemical Ionization |
| Cs$_2$CO$_3$ | Cesium carbonate |
| DCM | Dichloromethane |
| DMF | N,N-dimethylfomamide |
| DMSO | Dimethyl sulfoxide |
| DTT | Dithiothreitol |
| EDTA | Ethylenediaminetetraacetic acid |
| EIS | Electrospray ionization |
| EtOAc | Ethyl acetate |
| GSK3 | Glycogen synthase kinase 3 |
| HBSS | Hank's Balanced Salt solution |
| HCl | Hydrochloride |
| HEPES | 4-(2-Hydroxyethyl)-1-piperazine ethane sulfonic acid |
| HPLC | High Pressure Liquid Chromatography |
| KOH | Potassium hydroxide |
| LC-MS | Liquid Chromatography Mass Spectrometry |
| MeOH | Methanol |
| MES | 2-(N-Morpholino)ethanesulfonic acid |
| Mg(Ac)$_2$ | Magnesium Acetate |
| MOPS | Morpholinepropanesulfonic acid |
| NaHCO$_3$ | Sodium hydrogencarbonate |
| Na$_2$SO$_4$ | Sodium sulphate |
| NaOH | Sodium hydroxide |
| NH$_4$Cl | Ammonium chloride |
| Pd$_2$dba$_3$ | Tris-(dibenzylideneacetone)dipalladium(0) |
| PBS | Phosphate Buffered Saline |
| PMSF | Phenylmethylsulphonyl fluoride |
| RT | Room temperature |
| SPA | Scintillation Proximity Assay |
| THF | Tetrahydrofurane |
| TMS | Tetramethylsilane |
| UV | Ultra Violet |
| UV-DAD | Ultra Violet-Diod Array Detector |
| X-Phos | 2-Dicyclohexylphosphino-2',4',6'-triisopropylbiphenyl |

The invention claimed is:

1. A compound N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine of the formula (I)

(I)

or a pharmaceutically acceptable salt thereof.

2. A pharmaceutically acceptable salt according to claim 1 which is N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine disuccinate.

3. A pharmaceutically acceptable salt according to claim 1 which is N-(2,5-difluoro-4-(morpholinomethyl)phenyl)-5-fluoro-4-(2-methyl-1-(tetrahydro-2H-pyran-4-yl)-1H-imidazol-5-yl)pyrimidin-2-amine hemisuccinate.

4. A pharmaceutical composition comprising as active ingredient a therapeutically effective amount of a compound of formula (I) or a pharmaceutically acceptable salt thereof as claimed in claim 1 in association with at least one pharmaceutically acceptable adjuvant, diluent or carrier.

5. A pharmaceutical composition comprising as active ingredient a therapeutically effective amount of a pharmaceutically acceptable salt as claimed in claim 2 in association with at least one pharmaceutically acceptable adjuvant, diluent or carrier.

6. A pharmaceutical composition comprising as active ingredient a therapeutically effective amount of a pharmaceutically acceptable salt as claimed in claim 3 in association with at least one pharmaceutically acceptable adjuvant, diluent or carrier.

\* \* \* \* \*